United States Patent
Krüger et al.

(10) Patent No.: US 6,407,098 B1
(45) Date of Patent: Jun. 18, 2002

(54) FUNGICIDAL AZA-HETEROCYCLOALKENES

(75) Inventors: Bernd-Wieland Krüger, Bergisch Gladbach; Ulrich Heinemann, Leichlingen; Herbert Gayer, Monheim; Lutz Assmann, Eutin; Ralf Tiemann, Leverkausen; Thomas Seitz, Langenfeld; Gerd Hänssler, Leverkusen; Klaus Stenzel, Düsseldorf; Stefan Dutzmann, Langenfeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/702,551

(22) Filed: Oct. 31, 2000

Related U.S. Application Data

(62) Division of application No. 08/875,908, filed as application No. PCT/EP96/00384 on Jan. 31, 1996, now Pat. No. 6,214,825.

(30) Foreign Application Priority Data

Feb. 13, 1995 (DE) .......................................... 195 04 625
Mar. 22, 1995 (DE) .......................................... 195 10 297

(51) Int. Cl.$^7$ ........................ C07D 291/06; A01N 43/32
(52) U.S. Cl. ......................................... 514/222.5; 544/3
(58) Field of Search ............................. 544/3; 514/222.5

(56) References Cited

FOREIGN PATENT DOCUMENTS

| DE | A 44 08 005 | 2/1995 |
| EP | A 0 104 940 | 4/1984 |
| WO | WO 94/22844 | 10/1994 |
| WO | WO 99/57116 | * 11/1999 |

OTHER PUBLICATIONS

WO 95/26956 (Shionogi and Co., Ltd.), Oct. 12, 1995, Chemical Absracts, vol. 124, No. 11, Mar. 11, 1996, Columbus, Ohio, U.S., Abstract No. 14615f, p. 1258.

Database Crossfire, Beilstein Informationsysteme GmbH, Frankfurt DE, XP002001737, Siehe BRN=6407504 & Helv. Chim. Acta, vol. 3, No. 4, 1980, pp. 841–859.

Database Crossfire, Beilstein Informationsysteme, GmbH, Franfurt DE, XP 002001737, Siehe BRN=6407690 & Helv. Chim. Acta, vol. 63, No. 4, 1980, pp. 841–859.

Database Crossfire, Beilstein Informationsysteme GmbH, Franfurt DE, XP002001737, Siehe BRN=6416104 & Helv. Chim. Acta, vol. 63, No. 4, 1980, pp. 841–859.

Database Crossfire, Beilstein Informationsysteme GmbH, Franfurt DE, XP002001738, Siehe BRN=4188118 & Indian J. Chem. Sect. B., vol. 29, No. 4, 1990, pp. 315–318.

Database Crossfire, Beilstein Informationsysteme GmbH, Franfurt DE, XP002001738, Siehe BRN=4190136 & Indian J. Chem. Sect. B., vol. 29, No. 4, 1990, oo. 315–318.

Database Crossfire, Beilstein Informationsysteme GmbH, Franfurt DE, XP002001739, Siehe BRN=191959 & J. Indian Chem. Soc., vol. 6, 1929, pp. 106, 107.

Database Crossfire, Beilstein Informationsysteme GmbH, Franfurt DE, XP002001739, Siehe BRN=87414 & J. Indian Chem. Soc., vol. 6, 1929, pp. 106, 107.

Database Crossfire, Beilstein Informationsysteme GmbH, Franfurt DE, XP002001740, Siehe BRN=192293 & J. Indian. Chem. Soc., vol. 7, 1930, pp. 961, 964.

Database Crossfire, Beilstein Informationsysteme GmbH, Franfurt DE, XP002001741, Siehe BRN=218864 & J. Amer. Chem. Soc., vol. 47, 1925, p. 389.

Database Crossfire, Beilstein Informationsysteme GmbH, Franfurt DE, XP002001742, Siehe BRN=5071103 & Synthesis., vol. 12, 1989, pp. 923–929.

Database Crossfire, Beilstein Informationsysteme GmbH, Franfurt DE, XP002001743, Siehe BRN=191960 & J. Indian Inst. Sci., vol. 16, 1933, pp. 11, 17.

* cited by examiner

*Primary Examiner*—Bruck Kifle
(74) *Attorney, Agent, or Firm*—Norris McLaughlin & Marcus

(57) ABSTRACT

The application relates to novel heterocycloalkenes, to a number of processes for their preparation and to their use as fungicide.

6 Claims, No Drawings

FUNGICIDAL AZA-HETEROCYCLOALKENES

This application is a divisional of U.S. Ser. No. 08/875,908, filed on Aug. 6, 1997 now U.S. Pat. No. 6,214,825, and now allowed, which is, in turn, a 371 of PCT/EP96/00384, filed on Jan. 31, 1996.

The invention relates to novel substituted heterocycloalkenes, to a number of processes for their preparation and to their use as fungicides, and to novel intermediates and to a number of processes for their preparation.

It is known that certain substituted heterocyclic compounds possess fungicidal properties (cf. e.g. WO-A 9422844). However, the action of these compounds, especially at low application rates, is not entirely satisfactory in all areas of application.

The novel substituted heterocycloalkenes have now been found of the general formula (I)

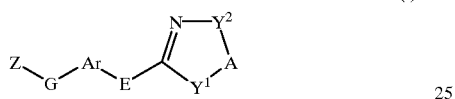

(I)

in which
  A represents optionally substituted alkylene,
  Ar represents optionally substituted arylene or heteroarylene,
  E represents a 1-alkene-1,1-diyl grouping which in position 2 contains a radical $R^1$, or represents a 2-aza-1-alkene-1,1-diyl grouping which in position 2 contains a radical $R^2$, or represents an optionally substituted imino grouping ("azamethylene", N—$R^3$), or represents a 3-aza-1-propene-2,3-diyl grouping which contains in position 1 a radical $R^1$ and in position 3 a radical $R^3$, or represents a 3-oxa-1-propene-2,3-diyl grouping which contains in position 1 a radical $R^1$, or represents a 3-thia-1-propene-2,3-diyl grouping which contains in position 1 a radical $R^1$, or represents a 1-aza-1-propene-2,3-diyl grouping which contains in position 1 a radical $R^2$ and in position 3 a radical $R^3$, or represents a 1-aza-1-propene-2,3-diyl grouping which contains in position 1 a radical $R^1$ and in position 3 a radical $R^3$, or represents a 1,3-diaza-1-propene-2,3-diyl grouping which contains in position 1 a radical $R^2$ and in position 3 a radical $R^3$ or represents a 1-aza-3-oxa-1-propene-2,3-diyl grouping which contains in position 1 a radical $R^2$, or represents a 1-aza-3-thia-1-propene-2,3-diyl grouping which contains in position 1 a radical $R^2$, where
    $R^1$ represents hydrogen, halogen, cyano or in each case optionally substituted alkyl, alkoxy, alkylthio, alkylamino or dialkylamino,
    $R^2$ represents hydrogen, amino, hydroxyl, cyano or in each case optionally substituted alkyl, alkoxy, alkylamino or dialkylamino, and
    $R^3$ represents hydrogen, cyano, hydroxyl or in each case optionally substituted alkyl, alkoxy, alkoxyalkyl, alkenyl, alkinyl, cycloalkyl or cycloalkylalkyl,
  G represents a single bond, oxygen, sulphur or represents alkanediyl, alkenediyl or alkinediyl each of which is optionally substituted by halogen, hydroxyl, alkyl, halogenoalkyl or cycloalkyl, or represents one of the following groupings —Q—CQ—, —CQ—Q—, —$CH_2$—Q—; —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—, —C($R^4$)=N—O—$CH_2$—, —N($R^5$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ—, —Q—, —CQ—N($R^5$)—CQ—Q—, —N($R^5$)—CQ—Q—$CH_2$—, —Q—C($R^4$)=N—O—$CH_2$—, —N($R^5$)—C($R^4$)=N—O—$CH_2$—, —O—$CH_2$—C($R^4$)=N—O—$CH_2$—, —N=N—C($R^4$)=N—O—$CH_2$—, —T—$Ar^1$— or —T—$Ar^1$—Q—, where
  $Ar^1$ represents optionally substituted arylene, heteroarylene, cycloalkylene, or heterocycloalkylene (i.e. a divalent aliphatic ring in which one or more carbon atoms are replaced by heteroatoms, i.e. atoms other than carbons.
  n represents the numbers 0, 1 or 2,
  Q represents oxygen or sulphur,
  $R^4$ represents hydrogen, cyano or in each case optionally substituted alkyl, alkoxy, alkylthio, alkylamino, dialkylamino or cycloalkyl, and
  $R^5$ represents hydrogen, hydroxyl, cyano or in each case optionally substituted alkyl, alkoxy or cycloalkyl, and
  T represents a single bond, oxygen, sulphur, —$CH_2$—O—, —$CH_2$—S— or optionally substituted alkanediyl,
  $Y^1$ represents oxygen, sulphur, or an optionally alkyl-substituted imino grouping ("azamethylene", NH, N-alkyl),
  $Y^2$ represents oxygen, or an optionally alkyl-substituted imino grouping ("azamethylene", NH, N-alkyl),
    where $Y^1$ and $Y^2$ do not simultaneously represent oxygen, and
  Z represents in each case optionally substituted alkyl, alkenyl, alkinyl, cycloalkyl, aryl or heterocyclyl.

Aryl represents aromatic, mono- or polycyclic hydrocarbon rings, for example phenyl, naphthyl, anthryl, phenanthryl, preferably phenyl or naphthyl, especially phenyl.

Heterocyclyl represents saturated or unsaturated, and aromatic, cyclic compounds in which at least one ring member is a heteroatom, i.e. an atom other than carbon. If the ring comprises two or more heteroatoms, they can be identical or different. Heteroatoms are preferably oxygen, nitrogen or sulphur. The cyclic compounds may form a polycyclic ring system together with further carbocyclic or heterocyclic, fused-on or bridge-connected rings. Preferred systems are mono- or bicyclic ring systems, especially mono- or bicyclic aromatic ring systems.

It has also been found that the novel substituted heterocycloalkenes of the general formula (I) are obtained if
  a) hydroxyl compounds of the general formula (II)

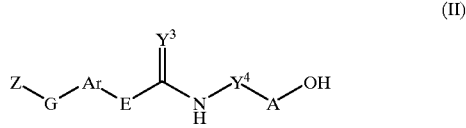

(II)

in which
  A, Ar, E, G and Z have the meaning given above and where

Y³ represents oxygen, sulphur or an optionally alkyl-substituted imino grouping ("azamethylene", NH, N-alkyl), and Y⁴ represents oxygen, or an optionally alkyl-substituted imino grouping ("azamethylene", NH, N-alkyl), are reacted with a sulphurizing reagent and/or a condensing agent, optionally in the presence of a diluent, or if b) nitrogen-containing carboxylic acid derivatives of the general formula (III)

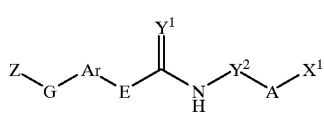

(III)

in which

A, Ar, E, G, Y¹, Y² and Z have the meaning given above, and

X¹ represents halogen, arylsulfonyl or alkylsulfonyl are reacted with an acid acceptor, optionally in the presence of a diluent.

Finally it has been found that the novel substituted heterocycloalkenes of the general formula (I) show a very strong fungicidal action.

The compounds according to the invention can if appropriate be present as mixtures of different possible isomeric forms, especially of stereoisomers, for example E and Z isomers, if appropriate also of tautomers. The claimed subject-matter comprises both the E isomers and the Z isomers, any desired mixtures of these isomers, and the possible tautomeric forms.

The invention preferably provides compounds of the formula (I) in which

A represents alkylene having 1 to 4 carbon atoms,

Ar represents in each case optionally substituted phenylene or naphthylene, or represents mono- or bicyclic heteroarylene having in each case 5 or 6 ring members, or represents benzo-fused heteroarylene having 5 or 6 ring members of which in each case at least one represents oxygen, sulphur or nitrogen and optionally one or two others represent nitrogen, the possible substituents preferably being selected from the following list:

Halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulfonyloxy, hydroxyiminoalkyl or alkoximinoalkyl having in each case 1 to 6 carbon atoms in the individual alkyl moieties, in each case divalent alkylene or dioxyalkylene having in each case 1 to 6 carbon atoms and being in each case optionally substituted by one or more identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms, E represents one of the following groupings:

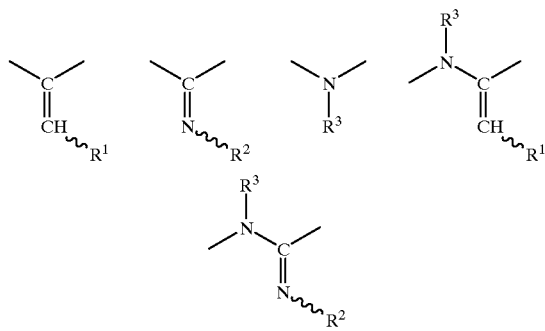

in which

R¹ represents hydrogen, halogen, cyano or in each case optionally halogen-, cyano- or $C_1$–$C_4$-alkoxy-substituted alkyl, alkoxy, alkylthio, alkylamino or dialkylamino having in each case 1 to 6 carbon atoms in the alkyl radicals, R² represents hydrogen, amino, hydroxyl, cyano or in each case optionally halogen-, cyano- or $C_1$–$C_4$-alkoxy-substituted alkyl, alkoxy, alkylamino or dialkylamino having in each case 1 to 6 carbon atoms in the alkyl radicals, R³ represents hydrogen, cyano, hydroxyl or in each case optionally halogen- or cyano-substituted alkyl, alkoxy, alkoxyalkyl, alkenyl or alkinyl having in each case up to 6 carbon atoms, or represents in each case optionally halogen-, cyano-, $C_1$–$C_4$-alkyl- or $C_1$–$C_4$-alkoxy-substituted cycloalkyl or cycloalkylalkyl having 3 to 6 carbon atoms in the cycloalkyl moiety and if appropriate 1 to 4 carbon atoms in the alkl moiety, G represents a single bond, oxygen, sulphur or represents alkanediyl, alkenediyl. alkinediyl having in each case up to 4 carbon atoms, in each case optionally substituted by halogen, hydroxyl, $C_1$–$C_4$-alkyl, $C_1$–$C_4$-halogenoalkyl or $C_3$–$C_6$-cycloalkyl, or represents one of the following groupings —Q—CQ—, —CQ—Q—, —CH₂—Q—; —Q—CH₂—, —CQ—Q—CH₂—, —CH₂—Q—CQ—, —Q—CH—CH₂—, —Q—CQ—Q—CH₂—, —N=N—, —S(O)ₙ—, —CH₂—S(O)ₙ—, —CQ—, —S(O)ₙ—CH₂—, —C(R⁴)=N—O—, —C(R⁴)=N—O—CH₂—, —N(R⁵)—, —CQ—N(R⁵)—, —N(R⁵)—CQ—, —Q—CQ—N(R⁵)—, —N=C(R⁴)—CH₂—, —CH₂—O—N=C(R⁴)—, —N(R⁵)—CQ—Q—, —CQ—N(R⁵)—CQ—O—, —N(R⁵)—CQ—Q—CH₂—, —Q—C(R⁴)=N—O—CH₂—, —N(R⁵)—C(R⁴)=N—O—CH₂—, —O—CH₂—C(R⁴)=N—O—CH₂—, —N=N—C(R⁴)=N—O—CH₂—, —T—Ar¹— or —T—Ar¹—Q—, where n represents the numbers 0, 1 or 2, Q represents oxygen or sulphur, R⁴ represents hydrogen, cyano, in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups, or represents in each case optionally halogen-, cyano-, carboxyl-, $C_1$–$C_4$-alkyl- or $C_1$–$C_4$-alkoxycarbonyl-substituted cycloalkyl having 3 to 6 carbon atoms, and $R^5$ represents hydrogen, hydroxyl, cyano or optionally halogen-, cyano- or $C_1$–$C_4$-alkoxy-substituted alkyl having 1 to 6 carbon atoms or represents optionally halogen-, cyano-, carboxyl-, $C_1$–$C_4$-alkyl- or $C_1$–$C_4$-alkoxy-carbonyl-substituted cycloalkyl having 3 to 6 carbon atoms, and $Ar^1$ represents phenylene, naphthylene or cycloalkylene each of which is optionally substituted one or more times by identical or different constituents, or represents heteroarylene or heterocycloalkylene having 3 to 7 ring members of which at least one represents oxygen, sulphur or nitrogen and if appropriate one or two further of which represent nitrogen, the possible substituents preferably being selected from the following list:

halogen, cyano, nitro, amino, hydroxyl, formyl, carboxyl, carbamoyl, thiocarbamoyl;

in each case straight-chain or branched alkyl, alkoxy, alkylthio, alkylsulfinyl or alkylsulfonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulfonyloxy, hydroxyiminoalkyl or alkoximinoalkyl having in each case 1 to 6 carbon atoms in the individual alkyl moiety, and cycloalkyl having 3 to 6 carbon atoms and T represents a single bond, oxygen, sulphur, —CH$_2$—O—, —CH$_2$—S— or represents alkanediyl having 1 to 3 carbon atoms, $Y^1$ represents oxygen sulphur, or an imino grouping which is optionally substituted by alkyl having 1 to 3 carbon atoms ("azamethylene", NH, N—$C_1$–$C_3$-alkyl), $Y^2$ represents oxygen, or an imino grouping which is optionally substituted by alkyl having 1 to 3 carbon atoms ("azamethylene", NH, N—$C_1$–$C_3$-alkyl), where $Y^1$ and $Y^2$ do not simultaneously represent oxygen, and Z represents alkyl having 1 to 8 carbon atoms which is optionally substituted one or more times by identical or different substituents consisting of halogen, cyano, hydroxyl, amino, $C_1$–$C_4$-alkoxy, $C_1$–$C_4$-alkylthio, $C_1$–$C_4$-alkylsulfinyl or $C_1$–$C_4$-alkylsulfonyl (each of which can optionally be substituted by halogen); or represents in each case optionally halogen-substituted alkenyl or alkinyl having in each case up to 8 carbon atoms; or represents cyloalkyl having 3 to 6 carbon atoms which is optionally substituted one or more times by identical or different substituents consisting of 15 halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl; or represents phenyl or naphthyl each of which is optionally substituted one or more times by identical or different substituents, or represents heterocyclyl having 3 to 7 ring members of which at least one represents oxygen, sulphur or nitrogen and optionally one or two further members thereof represent nitrogen, the possible substituents preferably being selected from the following list:

halogen, cyano, nitro, amino, hydroxyl, formyl, carboxyl, carbamoyl, thiocarbamoyl;

in each case straight-chain or branched alkyl, alkoxy, alkylthio, alkylsulfinyl or alkylsulfonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulfonyloxy having in each case 1 to 6 carbon atoms in the individual alkyl moieties;

in each case divalent alkylene or dioxyalkylene having in each case 1 to 6 carbon atoms, each of which is optionally substituted one or more times by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members of which in each case 1 to 3 are identical or different heteroatoms—especially nitrogen oxygen or sulphur—or a group

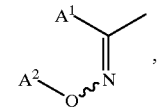

in which $A^1$ represents alkyl having 1 to 4 carbon atom or cycloalkyl having 1 to 6 carbon atoms, and $A^2$ represents optionally cyano-, alkoxy-, alkylthio-, alkylamino-, dialkylamino- or phenyl-substituted alkyl having 1 to 4 carbon atoms, alkenyl or alkinyl having in each case 1 to 4 carbon atoms.

In the definitions the saturated or unsaturated hydrocarbon chains, such as alkyl, alkanediyl, alkenyl or alkinyl, both alone and in conjunction with heteroatoms, such as in alkoxy, alkylthio or alkylamino, are in each case straight-chain or branched.

Halogen represents in general fluorine, chlorine, bromine or iodine, preferably fluorine, chlorine or bromine and especially fluorine or chlorine.

The invention relates in particular to compounds of the formula (I) in which

A represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-i-butylene, Ar represents in each case optionally substituted ortho-, meta- or para-phenylene, or represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (especially pyridine-2,3-diyl), pyrimidinediyl, pyridazinediyl, pyrazinediyl, 1,3,4triazinediyl or 1,2,3-triazinediyl, the possible substituents being selected in particular from the following list: Fluorine, chlorine, cyano, methyl, ethyl, cyclopropyl, trifluoromethyl, methoxy, ethoxy, methylthio, methylsulfinyl or methylsulfonyl, E represents one of the following groupings:

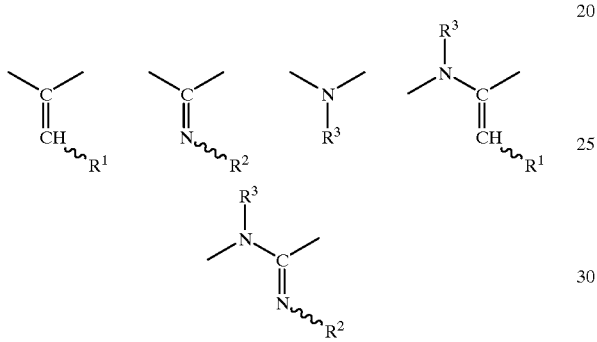

in which $R^1$ represents hydrogen, fluorine, chlorine, bromine, cyano or represents in each case optionally fluorine-, chlorine-, cyano-, methoxy- or ethoxy-substituted methyl, ethyl, propyl, methoxy, ethoxy, methylthio, ethylthio, methylamino, ethylamino or dimethylamino, $R^2$ represents hydrogen, amino, hydroxyl, cyano or represents in each case optionally fluorine-, chlorine-, cyano-, methoxy- or ethoxy-substituted methyl, ethyl, methoxy, ethoxy, methylamino, ethylamino or dimethylamino $R^3$ represents hydrogen, cyano or represents in each case optionally fluorine-, chlorine- or cyano-substituted methyl, ethyl, n- or i-propyl, n-, i- or s-butyl, methoxy, ethoxy or methoxymethyl, or represents allyl or propargyl, or represents in each case optionally fluorine-, chlorine-, cyano-, methyl-, ethyl-, n- or i-propyl, methoxy- or ethoxy-substituted cyclopropyl, cyclobutyl, cyclopentyl, cyclohexyl, cyclopropylmethyl, cyclobutylrnethyl, cyclopentylmethyl or cyclohexylmethyl, G represents a single bond, oxygen, sulphur or represents methylene, dimethylene (ethane-1,2-diyl), ethene-1,2-diyl, ethine-1,2diyl, each of which is optionally substituted by fluorine, chlorine, bromine, hydroxyl, methyl, ethyl, n- or i-propyl, trifluoromethyl, cyclopropyl, cyclobutyl, cyclopentyl or cyclohexyl, or represents one of the following groupings
—Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N═N—, —S(O)$_n$—, —CH$_2$—S(O)$_n$—, —CQ—, —S(O)$_n$—CH$_2$—, —C(R$^4$)═N—O—, —C(R$^4$)═N—O—CH$_2$—, —N(R$^5$)—, —CQ—N(R$^5$)—, —N(R$^5$)—CQ—, —Q—CQ—N(R$^5$)—, —N═C(R$^4$)—Q—CH$_2$—, —CH$_2$—O—N═C(R$^4$)—, —N(R$^5$)—CQ—Q—, —CQ—N(R$^5$)—CQ—Q—, —N(R$^5$)—CQ—Q—CH$_2$—, —Q—C(R$^4$)═N—O—CH$_2$—, —N(R$^5$)—C(R$^4$)═N—O—CH$_2$—, —O—CH$_2$—C(R$^4$)═N—O—CH$_2$—, —N═N—C(R$^4$)═N—O—CH$_2$—, —T—Ar$^1$— or —T—Ar$^1$—Q—, where n represents the numbers 0, 1 or 2, Q represents oxygen or sulphur $R^4$ represents hydrogen, cyano, in each case optionally fluorine-, chlorine-, cyano-, methoxy- or ethoxy-substituted methyl, ethyl, n- or i-propyl, n-. i- or s-butyl, methoxy, ethoxy, propoxy, butoxy, methylthio, ethylthio, propylthio, butylthio, methylamino, ethylamino, propylamino, dimethylamino or diethylamino, or represents cyclopropyl, cyclobutyl, cyclopentyl or cyclohexyl each of which is optionally substituted by fluorine, chlorine, cyano, carboxyl, methyl, ethyl, n- or i-propyl, methoxycarbonyl or ethoxycarbonyl, and $R^5$ represents hydrogen, hydroxyl, cyano or represents in each case optionally fluorine-, chlorine-, cyano-, methoxy- or ethoxy-substituted methyl, ethyl, n- or i-propyl, n-, i-, s- or t-butyl, or represents cyclopropyl, cyclobutyl, cyclopentyl or cyclohexyl each of which is optionally substituted by fluorine, chlorine, cyano, carboxyl, methyl, ethyl, n- or i-propyl, methoxy-carbonyl or ethoxy-carbonyl, Ar$^1$ represents in each case optionally mono- to trisubstituted phenylene, naphthylene, furandiyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4triazinediyl, 1,3,5-triazinediyl, oxirandiyl, oxetanediyl, tetrahydrofurandiyl, perhydropyrandiyl or pyrrolidinediyl, the possible substituents preferably being selected from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl, ethoximinoethyl or cyclopropyl, and T represents a single bond, oxygen, sulphur, —CH$_2$—O—, —CH$_2$—S—, methylene, ethylene or propylene, and $Y^1$ represents oxygen, sulphur, —NH—, —N(CH$_3$)— or —N(C$_2$H$_5$)—, $Y^2$ represents oxygen, —NH—, —N(CH$_3$)— or —N(C$_2$H$_5$)—, where $Y^1$ and $Y^2$ do not simultaneously represent oxygen, and Z represents methyl, ethyl, n- or i-propyl, n-, i-, s- or t-butyl, each of which is optionally substituted one to five times by fluorine, chlorine, bromine, cyano, hydroxyl, amino, methoxy, ethoxy, methylthio, ethylthio, methylsulfinyl, ethylsulfinyl, methylsulfonyl, ethylsulfonyl (which are each optionally substituted by fluorine and/or chlorine);

or represents allyl, crotonyl, 1-methyl-allyl, propargyl or 1-methyl-propargyl each of which is optionally substituted one to three times by fluorine, chlorine or bromine;

or represents cyclopropyl, cyclobutyl, cyclopentyl or cyclohexyl, each of which is optionally substituted one to six times by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

or represents in each case optionally mono- to trisubstituted phenyl, naphthyl, furyl, thienyl, oxazolyl, isoxazolyl, thiazolyl, isothiazolyl, 1,2,4-oxadiazolyl, 1,3,4-oxadiazolyl, 1,2,4-thiadiazolyl, 1,3,4-thiadiazolyl, pyridinyl, pyrimidinyl, pyridazinyl, pyrazinyl, 1,2,3-triazinyl, 1,2,4triazinyl, 1,3,5-triazinyl, oxiranyl, oxetanyl, tetrahydrofuryl, perhydropyranyl, pyrrolidinyl, piperidinyl or morpholinyl, the possible substituents preferably being selected from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n-or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl, methylamino, ethylamino, n- or i-propylamino, dimethylamino, diethylamino. acetyl, propionyl, acetyloxy, methoxycarbonyl, ethoxycarbonyl, methylsulfonyloxy, ethylsulfonyloxy;

or represents in each case divalent trimethylene (propane-1,3-diyl), methylenedioxy or ethylenedioxy, each of which is optionally substituted one or more times by identical or different substituents consisting of fluorine, chlorine, methyl, trifluoromethyl, ethyl, n- or i-propyl, cyclopropyl, cyclobutyl, cyclopentyl or cyclohexyl, or a grouping

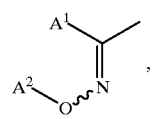

in which
A¹ represents methyl, ethyl, n- or i-propyl, n-, i-, s- or t-butyl, cyclopropyl or cyclobutyl and
A² represents methyl, ethyl, n- or i-propyl, n-, i-, s- or t-butyl, allyl, propargyl, but-2-ene-1-yl, 2-methyl-prop-1-ene-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

Very particularly preferred compounds of the general formula (I) are those in which
A represents methylene, 1,1,-ethylene, 1,2-ethylene, 1,2- or 1,3-propylene,
Ar represents ortho-phenylene, pyridine-2,3-diyl or thiophene-2,3-diyl,
E represents one of the following groupings

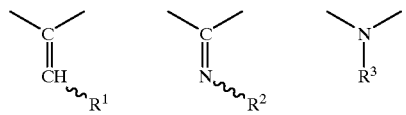

in which
R¹ and R² each represent methoxy, and
R³ represents hydrogen, cyano, methyl, ethyl, n- or i-propyl, methoxy or ethoxy, G represents oxygen or represents in each case optionally fluorine-, chlorine- or bromine-substituted dimethylene (ethane-1,2-diyl), ethene-1,2-diyl or one of the following groupings —Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N=N—, —S(O)ₙ—, —CH₂—S(O)ₙ—, —CQ—, —S(O)ₙ—CH₂—, —C(R⁴)=N—O—, —C(R⁴)=N—O—CH₂—, —N(R⁵)—, —CQ—N(R⁵)—, —N(R⁵)—CQ—, —Q—CQ—N(R⁵)—, —N=C(R⁴)—Q—CH₂—, —CH₂—O—N=C(R⁴)—Q—, —N(R⁵)—CQ—Q—, —CQ—N(R⁵)—CQ—, —N(R⁵)—CQ—Q—CH₂—, —Q—C(R⁴)=N—O—CH₂—, —N(R⁵)—C(R⁴)=N—O—CH₂—, —O—CH₂—C(R⁴)=N—O—CH₂—, —N=N—C(R⁴)=N—O—CH₂—, —T—Ar¹— or —T—Ar¹—Q—, where
n represents the numbers 0, 1 or 2,
Q represents oxygen or sulphur,
R⁴ represents hydrogen, cyano, methyl, ethyl or cyclopropyl, and
R⁵ represents hydrogen, methyl, ethyl or cyclopropyl,
Ar¹ represents phenylene or pyridinediyl each of which is optionally substituted one to three times by identical or different substituents, or represents in each case optionally monosubstituted pyrimidinediyl, pyridazinediyl, pyrazinediyl, 1,2,3-triazinediyl, 1,2,4triazinediyl or 1,3,5-triazinediyl, or represents 1,2,4thiadiazolediyl, 1,3,4thiadiazolediyl, 1,2,4oxadiazolediyl, 1,3,4,-oxadiazolediyl, the possible substituents preferably being selected from the following list:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, and T represents a single bond, oxygen, sulphur, —CH₂—, —CH₂—S—, methylene, ethylene or propylene, and
Y¹ represents oxygen, sulphur, —NH— or —N(CH₃)—, $Y^2$ represents oxygen, —NH— or —N(CH$_3$)—,
where $Y^1$ and $Y^2$ do not simultaneously represent oxygen, and Z represents phenyl, 1,2,4thiadiazolyl, 1,3,4thiadiazolyl, 1,2,4oxadiazolyl, 1,3,4oxadiazolyl, pyridinyl, pyrimidinyl, pyridazinyl, pyrazinyl, 1,2,3-triazinyl, 1,2,4triazinyl or 1,3,5-triazinyl, each of which is optionally substituted one to three times by identical or different substituents, the possible substituents preferably being selected from the following list:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methoxycarbonyl, ethoxycarbonyl, methoximinomethyl, ethoximinomethyl, methoximinoethyl, ethoximinoethyl, in each case divalent methylenedioxy or ethylenedioxy, each of which is optionally substituted one to four times by identical or different substituents consisting of fluorine, chlorine, methyl, trifluoromethyl or ethyl.

A particularly preferred group of compounds according to the invention are those compounds of the formula (I) in which A represents methylene, 1,1-ethylene, 1,2-ethylene, 1,2- or 1,3-propylene, Ar represents ortho-phenylene, pyridine-2,3-diyl or thiophene-2,3-diyl, E represents one of the following groupings

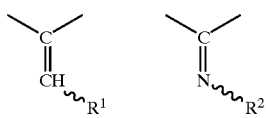

in which
$R^1$ and $R^2$ each represent methoxy, and

G represents —O—CH$_2$—, and $Y^1$ represents oxygen, sulphur, —NH— or —N(CH$_3$)—,
$Y^2$ represents oxygen, —NH— or —N(CH$_3$)—,
where $Y^1$ and $Y^2$ do not simultaneously represent oxygen, and Z represents phenyl which is optionally substituted one to three times by identical or different substituents, the possible substituents preferably being selected from the following list:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methoxycarbonyl, ethoxycarbonyl, in each case divalent methylenedioxy or ethylenedioxy, each of which is optionally substituted one to four times by identical or different substituents consisting of fluorine, chlorine, methyl, trifluoromethyl or ethyl, or a grouping

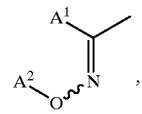

in which
$A^1$ represents methyl, ethyl, n- or i-propyl, n-, i-, s- or t-butyl, cyclopropyl or cyclobutyl, and
$A^2$ represents methyl, ethyl, n- or i-propyl, n-, i-, s- or t-butyl, allyl, propargyl, but-2-ene-1-yl, 2-methyl-prop-1-ene-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A likewise particularly preferred group of compounds according to the invention are those compounds of the formula (I)
in which A represents methylene, 1,1-ethylene, 1,2-ethylene, 1,2- or 1,3-propylene, Ar represents ortho-phenylene, pyridine-2,3-diyl or thiophene-2,3-diyl, E represents one of the following groups

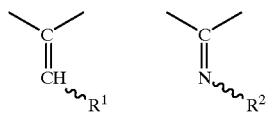

in which
$R^1$ and $R^2$ each represent methoxy, and

G represents —C(R$^4$)=N—O—CH$_2$—, where
$R^4$ represents hydrogen, cyano, methyl, ethyl or cyclopropyl, $Y^1$ represents oxygen, sulphur, —NH— or —N(CH$_3$)—,
$Y^2$ represents oxygen, —NH— or —N(CH$_3$)—,
where $Y^1$ and $Y^2$ do not simultaneously represent oxygen, and Z represents phenyl, pyridyl or pyrimidyl, each of which is optionally substituted one to three times by identical or different substituents, the possible substituents preferably being selected from the following list:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methoxycarbonyl, ethoxycarbonyl, methoximinomethyl, ethoximinomethyl, methoximinoethyl, ethoximinoethyl, in each case divalent methylenedioxy or ethylenedioxy, each of which is optionally substituted one to four times by identical or different substituents consisting of fluorine, chlorine, methyl, trifluoromethyl or ethyl.

An additionally particularly preferred group of compounds according to the invention are those compounds of the formula (I)
in which
A represents methylene, 1,1,-ethylene, 1,2-ethylene, 1,2- or 1,3-propylene,
Ar represents ortho-phenylene,
E represents one of the following groups

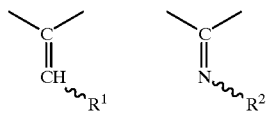

in which
R$^1$ and R$^2$ each represent methoxy, and
G represents T—Ar$^1$—Q—, where
Q represents oxygen or sulphur,
Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl, or 1,3,5-triazinediyl, each of which is optionally substituted one or two times by identical or different substituents consisting of fluorine, chlorine, cyano, methyl, cyclopropyl, methoxy, methylthio, trifluoromethyl, difluoromethoxy, trifluoromethoxy, difluorochloromethoxy,
T represents a single bond, oxygen, sulphur, —CH$_2$—O—, —CH$_2$—S—, methylene, ethylene or propylene, and Y$^1$ represents oxygen, sulphur, —NH— or —N(CH$_3$)—,
Y$^2$ represents oxygen, —NH— or —N(CH$_3$)—,
where Y$^1$ and Y$^2$ do not simultaneously represent oxygen, and
Z represents phenyl, pyridyl or thienyl, each of which is optionally substituted one to three times by identical or different substituents consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy, or by in each case divalent methylenedioxy or ethylenedioxy, each of which is optionally substituted one or more times by identical or different substituents consisting of fluorine, chlorine, methyl, trifluoromethyl or ethyl.

The general definitions of radicals listed above, or those indicated as being in preferred ranges, apply both to the end products of the formula (I) and also, correspondingly, to the particular starting substances and intermediates required for the preparation.

These definitions of radicals can be combined with one another as desired, thus including combinations between the stated ranges of preferred compounds.

Examples of the compounds according to the invention are listed in Tables 1 to 8:

TABLE 1

(IA)

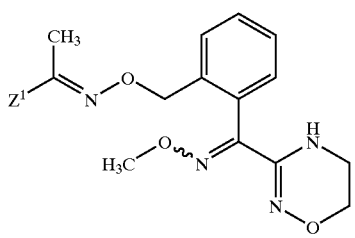

where Z$^1$ represents the following substituents:

| Z$^1$ | Z$^1$ | Z$^1$ | Z$^1$ | Z$^1$ | Z$^1$ |
|---|---|---|---|---|---|
|  |  |  | 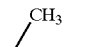 | 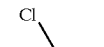 |  |
|  |  |  |  |  |  |
|  | 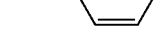 |  |  |  |  |

TABLE 1-continued
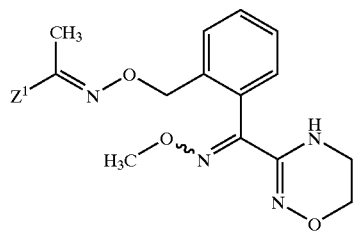
(IA)
where Z¹ represents the following substituents:
| Z¹ | Z¹ | Z¹ | Z¹ | Z¹ | Z¹ |
|---|---|---|---|---|---|
| 2-methylpyrimidin-4-yl O—CH₂CF₃ | 2-methylpyrimidin-4-yl OC₂H₅ | 2-methylpyrimidin-4-yl OC₃H₇-i | 2-methylpyrimidin-4-yl O—CH₂-cyclopropyl | 6-methylpyrimidin-4-yl O—CH₂CF₃ | |
TABLE 2
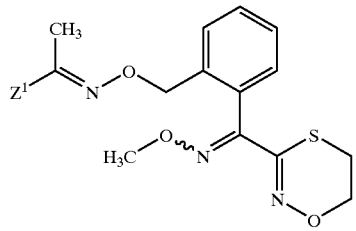
(IA-1)
where Z¹ represents the substituents cited in Table 1.

TABLE 3

(IB)

where $Z^2$ represents the following substituents:

TABLE 3-continued
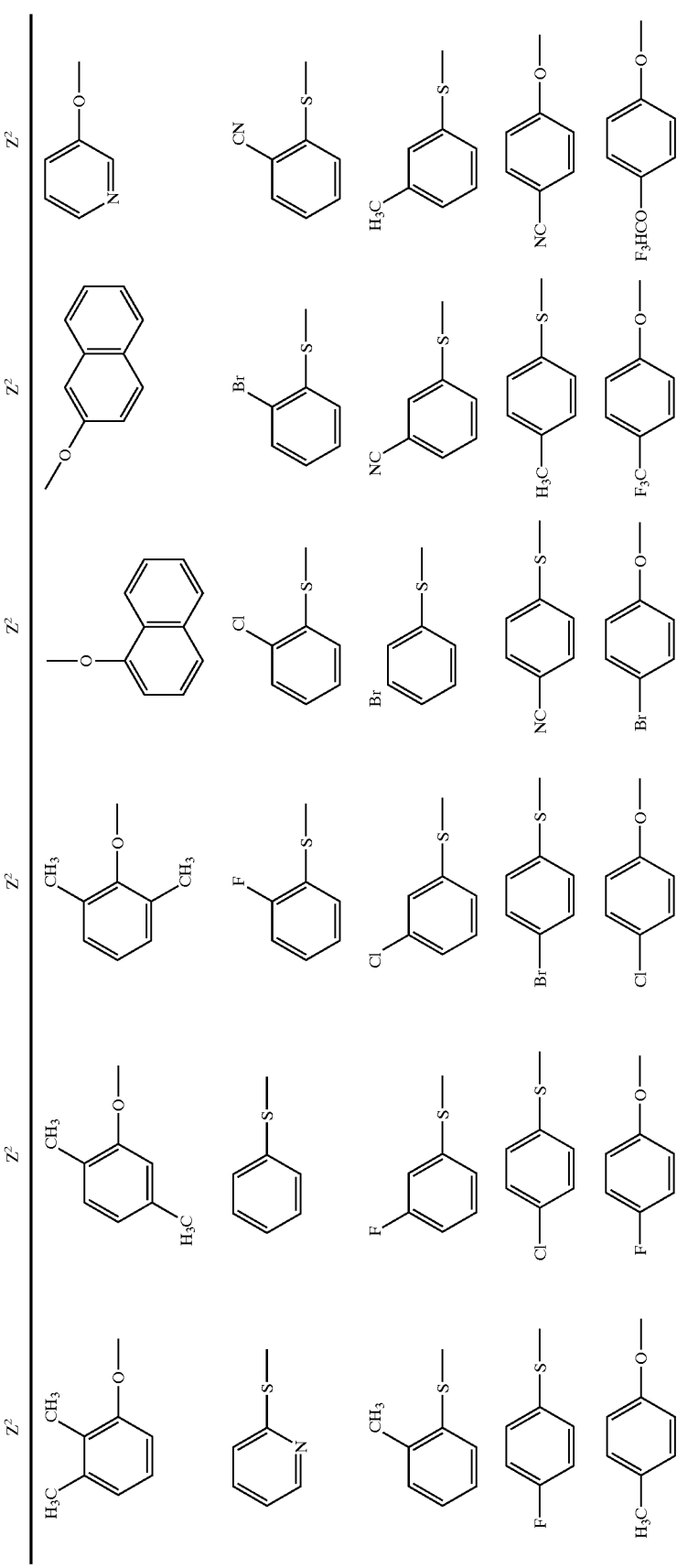
where $Z^2$ represents the following substituents:

TABLE 3-continued where Z² represents the following substituents:

TABLE 3-continued (IB)

where Z² represents the following substituents:

TABLE 4
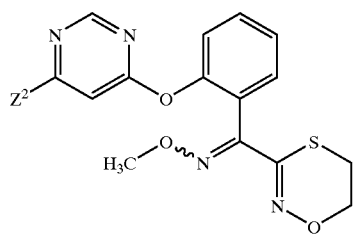
(IB-1)
where Z² represents the substituents cited in Table 3.
TABLE 5
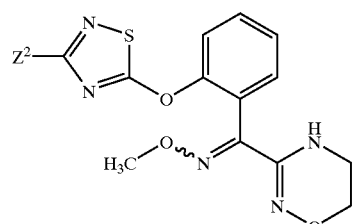
(IC)
where Z² represents the substituents cited in Table 3.
TABLE 6
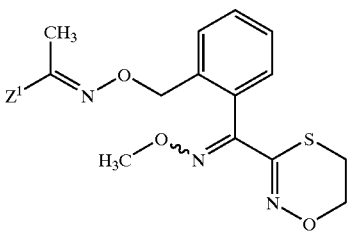
(IB-1)
where Z³ represents the substituents cited in Table 5.
TABLE 7
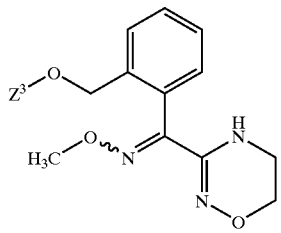
(IE)
where Z³ represents the following substituents:
| Z³ | Z³ | Z³ | Z³ | Z³ | Z³ |
|---|---|---|---|---|---|
| 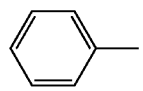 | 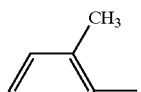 | 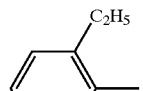 | 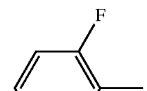 | 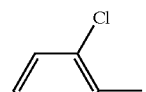 | 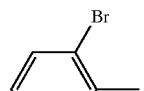 |
| 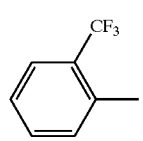 | 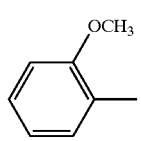 | 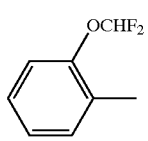 | 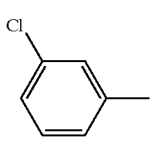 | 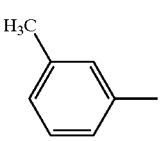 | 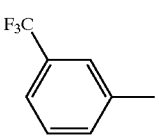 |
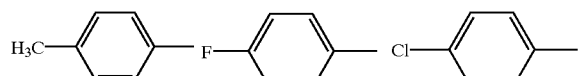
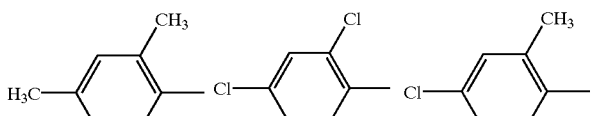

TABLE 7-continued (IE)

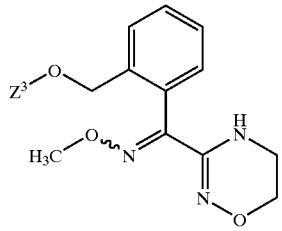

where $Z^3$ represents the following substituents:

[Structures of $Z^3$ substituents shown]

TABLE 8

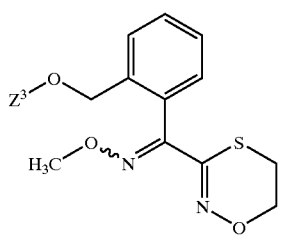

where $Z^3$ represents the substituents cited in Table 7.

A general definition of the hydroxyl compounds required as starting materials for carrying out process a) according to the invention is given by the formula (II). In this formula (II), A, Ar, E, G and Z preferably or in particular have that meaning which has already been indicated as being preferred or particularly preferred for A, Ar, E, G and Z in connection with the description of the compounds of the formula (I) according to the invention. $Y^3$ represents oxygen, sulphur, or an optionally alkyl-, preferably methyl-, ethyl-, n- or i-propyl-substituted imino grouping and $Y^4$ represents oxygen, or an optionally alkyl-, preferably methyl-, ethyl-, n- or i-propyl-substituted imino grouping.

The hydroxyl compounds of the formula (II) were not hitherto known; however, where $Y^3$ and $Y^4$ in the formula (II) simultaneously represent oxygen, they are the subject of an earlier application by us (see DE-A 4326908 of 11.8.93). Where $Y^3$ and $Y^4$ do not simultaneously represent oxygen, they are the subject of the present application.

It has additionally been found that the hydroxyl compounds of the general formula (II) likewise exhibit a very strong fungicidal action.

The hydroxyl compounds of the formula (II) are obtained (process a-1)), if carboxylic acid derivatives of the general formula (IV)

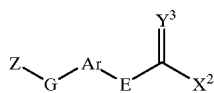

in which
Ar, E, G, $Y^3$ and Z have the meaning given above and
$X^2$ represents halogen or alkoxy
are reacted with a hydroxyalkyl compound of the formula (V)

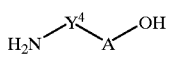

in which
A and $Y^4$ have the meaning given above,
optionally in the presence of a diluent, for example toluene, pyridine, dichloromethane or tetrahydrofuran and optionally in the presence of an acid acceptor, for example triethylamine, pyridine, dimethylaminopyridine, sodium hydroxide or potassium carbonate, at temperatures from −20 to 100° C., preferably from 0 to 80° C.

A general definition of the carboxylic acid derivatives required as starting materials for carrying out process a1) according to the invention for the preparation of the hydroxyl compounds of the general formula (II) is given by the formula (IV). In this formula (IV), Ar, E, G, $Y^3$ and Z preferably or in particular have that meaning which has already been indicated as being preferred or particularly preferred for Ar, E, G, $Y^3$ and Z in connection with the description of the compounds of the formula (I) according to the invention, or, respectively, of the hydroxy compounds of the formula (II). $X^2$ represents halogen, preferably chlorine, or represents alkoxy, preferably ethoxy or methoxy.

The carboxylic acid derivatives of the formula (IV) are known and/or can be prepared by methods which are known per se (cf. EP-A 178826, EP-A 242081, EP-A382375, EP-A 493711, EP-A 432503, DE-A 3938054, EP-A 528 681).

A general definition of the hydroxy alkyl compounds which are additionally required as starting materials for carrying out process a1) according to the invention for preparing the hydroxy compounds of the general formula (II) is given by the formula (V). In this formula (V), A and $Y^4$ preferably or in particular have that meaning which has already been indicated as being preferred or particularly preferred for A and $Y^4$ in connection with the description of the compounds of the formula (I) according to the invention, or, respectively, of the hydroxy compounds of the formula (II).

The hydroxyalkyl compounds of the formula (V) are known and/or can be prepared by methods which are known per se (cf. e.g. B. J. Chem. Soc., Chem. Com. 1986, 903 or J. Med. Chem. 1968, 504).

As sulphurization reagent for carrying out process a) according to the invention, suitable reagents are all those which are capable of exchanging oxygen for sulphur in a molecule, examples being hydrogen sulphide, phosphorus pentasulphide, Lawesson's Reagent.

Process a) according to the invention is optionally carried out in the presence of a suitable diluent. Suitable diluents for carrying out the process a) according to the invention are all inert organic solvents. These preferably include aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichioroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane.

Process a) according to the invention is optionally carried out in the presence of a suitable condensing agent. Suitable such agents are all customary reagents which are capable of eliminating water from a molecule. Examples are acid halide formers such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous oxide, polyphosphoric acid, N,N'-carbonyldiimidazole, 2-ethoxy-N-ethoxycarbonyl-1,2-dihydro-quinoline (EEDQ) or triphenyl phosphine/carbon tetrachloride.

When carrying out process a) according to the invention the reaction temperatures can be varied in a relatively wide range. It is in general carried out at temperatures between 0° C. and +200° C., preferably at temperatures between 10° C. and 140° C.

In order to carry out process a) according to the invention for the preparation of the compounds according to the formula (I), from 0.1 to 10 mol, preferably from 0.1 to 5 mol, of sulphurizing reagent are generally employed per mole of hydroxy compound of the formula (II).

A general definition of the nitrogen-containing carboxylic acid derivatives required as starting materials for carrying out process b) according to the invention is given by the formula (III). In this formula (III), A, Ar, E, G, $Y^1$, $Y^2$ and Z preferably or in particular have that meaning which has already been indicated as preferred or particularly preferred for A, Ar, E, G, $Y^1$, $Y^2$ and Z in connection with the description of the compounds of the formula (I) according to the invention. $X^1$ represents halogen, arylsulphonyl or alkylsulphonyl, preferably chlorine, methylsulphonyl or 4-tolylsulphonyl.

The nitrogen-containing carboxylic acid derivatives of the formula (III) have not been disclosed hitherto; as novel substances they are a subject of the present application.

It has additionally been found that the nitrogen-containing carboxylic acid derivatives of the formula (III) likewise exhibit a very strong fungicidal action.

The nitrogen-containing carboxylic acid derivatives of the formula (III) are obtained (process b-1)) if the hydroxy compounds of the formula (II), which have already been described above in connection with the preparation of the compounds of the formula (I) according to the invention by process a), are reacted with a halogenating agent, for example thionyl chloride, optionally in the presence of a diluent, for example toluene, xylene or chiorobenzene, optionally in the presence of a reaction auxiliary, for example dimethylformamide or pyridine, at temperatures from −20 to 120° C., preferably from 0 to 100° C., or with a sulphonyl halide, for example methanesulphonyl chloride or 4-toluene-sulphonyl chloride, optionally in the presence of a diluent, for example toluene, pyridine, dichloromethane or tetrahydrofuran, and optionally in the presence of an acid acceptor, for example triethylamine, pyridine, dimethylaminopyridine, sodium hydroxide or calcium carbonate, at temperatures from −20 to 120° C., preferably from 0 to 100° C.

The halogenating agents and/or sulphonyl halides which are additionally required as starting materials for carrying out process b-1) according to the invention for preparing the nitrogen-containing carboxylic acid derivatives of the general formula (II) are generally known reagents in organic chemistry.

As acid acceptors which are additionally required for carrying out process b) according to the invention, all customary inorganic or organic bases are suitable. Examples thereof include alkaline earth metal or alkali metal hydrides, hydroxides, amides, alcoholates, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as triethylamine, triethylamine, tributylamine, N,N-dimethylaniline, N,N-dimethylbenzylamine, pyridine. N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out process b) according to the invention are all inert organic solvents. These include preferably, aliphatic, alicyclic or aromatic hydrocarbons, for example petroleum ether, hexane, heptane, cyclohexane, methylcyclohexane, benzene, toluene, xylene or decal in; halogenated hydrocarbons, for example chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n-or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholanes; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water, or pure water.

When carrying out process b) according to the invention the reaction temperatures can be varied within a relatively wide range. It is generally carried out at temperatures between −20° C. and +130° C., preferably at temperatures between 0° C. and 100° C.

In order to carry out process b) according to the invention for preparing the compounds of formula (I), from 0.8 to 15 mol, preferably from 0.8 to 8 mol, of the acid acceptor are generally employed per mole of nitrogen-containing carboxylic acid derivative of the formula (II).

Processes a) and b) according to the invention are generally carried out under atmospheric pressure. However, it is also possible to operate under increased or reduced pressure, in general between 0.1 bar and 10 bar.

The reaction procedure and the working up and isolation of the reaction products are carried out by known methods (cf. also the Preparation Examples).

The active compounds according to the invention have a strong microbicidal action and are employed in practice for combating unwanted microorganisms. The active compounds are suitable for use as plant protection agents, especially as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, Pythium ultimum;

Phytophthora species, such as, for example, Phytophthora infestans; Pseudoperonospora species, such as, for example, Pseudoperonospora humuli or Pseudoperonospora cubensis;

Plasmopara species, such as, for example, Plasmopara viticola;

Peronospora species, such as, for example, Peronospora pisi or Peronospora brassicae;

Erysiphe species, such as, for example, Erysiphe grarninis;

Sphaerotheca species, such as, for example, Sphaerotheca fuliginea;

Podosphaera species, such as, for example, Podosphaera leucotricha;

Venturia species, such as, for example, Venturia inaequalis;

Pyrenophora species, such as, for example, Pyrenophora teres or Pyrenophora graminea (conidia form: Drechslera, synonym: Helminthosporium);

Cochliobolus species, such as, for example, Cochliobolus sativus (conidia form;

Drechslera, synonym: Helminthosporium);

Uromyces species, such as, for example, Uromyces appendiculatus;

Puccinia species, such as, for example, Puccinia recondita;

Tilletia species, such as, for example, Tilletia caries;

Ustilago species, such as, for example, Ustilago nuda or Ustilago avenae;

Pellicularia species, such as, for example, Pellicularia sasakii;

Pyricularia species, such as, for example, Pyricularia oryzae;

Fusarium species, such as, for example, Fusarium culmorum;

Botrytis species, such as, for example, Botrytis cinerea;

Septoria species, such as, for example, Septoria nodorum;

Leptosphaeria species, such as, for example, Leptosphaeria nodorum;

Cercospora species, such as, for example, Cercospora canescens;

Altemaria species, such as, for example, Altemaria brassicae and

Pseudocercosporella species, such as, for example, Pseudocercosporella herpotrichoides.

The good toleration, by plants, of the active compounds, at the concentrations required for combating plant diseases, permits treatment of the above-ground parts of plants, and treatment of vegetative propagation stock and seeds, and of the soil.

In this context, the active compounds according to the invention are employed with particular success to combat diseases in cereals, for example against Erysiphe species, or cereals in viticulture, fruit-growing and vegetable growing, for example against Venturia, Podosphaera amd Sphaerotheca species. The active compounds according to the invention also successfully combat diseases in rice, for example Pyricularia species.

Depending on their particular physical and/or chemical properties, the active compounds are, if desired, converted into customary formulations, such as, for example, solutions, emulsions, suspensions, powders, foams, pastes, granules, aerosols, very fine encapsulations in polymeric substances and in coating compositions for seed, and ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents. there are suitable in the main: aromatics, such as xylene, toluene or alkylnaphthalenes, chlorinated aromatics or chlorinatedliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, aiylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other possible additives are mineral and vegetable oils.

It is possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in their formulations, are also used as a mixture with known fungicides, bactericides, acaricides, nematicides or insecticides. for example to widen the spectrum of action or to prevent the build-up of resistance.

In many cases, synergistic effects are observed.

Examples of suitable components for the mixtures are:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzarnide; (E)-2-methoxyimino-N-methyl-2-(2-phenoxyphenyl) acetarnide; 8-hydroxyquinoline sulphate; methyl (E)2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazirn, carboxin, quinomethionate, chloroneb, chloropicrrn, chlorothalonil, chlozolinate, cufraneb, cymoxanil, cyproconazole, cyprofuram, dichlorophen, diclobutrazol, diclofluaaid, diclomezin, dicloran, diethofencarb, difenoconazole, dimethirimol, dimethomorph, diniconazole, dinocap, diphenylamine, dipyrithion, ditalimfos, ditianon, dodine, drazoxolon, edifenphos, epoxyconazole, ethirimol, etridiazole, fenarimol, fenbuconazole, fenfura, fenitropan, fenpiclonil, fenpropidin fenpropimorph, fentin acetate, fentin hydroxide, ferbam, ferimzone, fluazinam, fludioxonil, fluoromnide, fluquinconazole, flusilazole, flusulfaride, flutolanil, flutriafol, folpet, fosetyl-aluminiun, fthalide, fuberidazole, furalaxyl, furmecyclox, guazatine, hexachlorobenzene, hexaconazole, hymexazol, imazalil, imnibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture.

mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflurrizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin. clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazion, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothnn, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethnin triarathen, triazophos, triazuron, trichlorfon, triflumuron, trimethacarb, vamidothion, XMC, xylylcarb, YI 5301/5302, zetamethrin.

If desired, the active compounds according to the invention are also mixed with other known active compounds, such as herbicides, or else with fertilizers and growth regulators.

The active compounds are used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on, etc. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of the soil, active compound concentrations of 0.00001 to 0.1% by weight, preferably 0.0001 to 0.02% by weight, are required at the site of action.

PREPARATION EXAMPLES

Example (I-1)

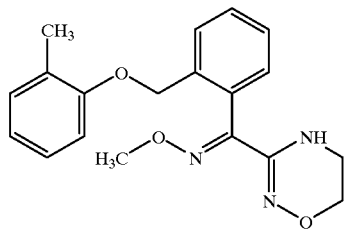

(Process b))

0.4 g (1.067 mmol) of 2-[2-(2-methylphenoxymethyl)-phenyl]-2-(methoximino)-O-(2-chloroethyl)acetamide oxime is dissolved in 10 ml of N-methylpyrrolidone, and 35 mg of sodium hydride (1.17 mmol; 80% strength in paraffin) are slowly added. The mixture is stirred at 100° C. for 16 h and poured into water, the aqueous mixture is subjected to multiple extraction with ethyl acetate, the extracts are again washed with water, the organic phase is dried over magnesium sulphate and the solvent is distilled off in vacuo. The residue is then chromatographed over silica gel (eluent toluene:acetone=15:1). 0.23 g (64% of theory) is obtained of 3-{1-[2-(2-methylphenoxymethyl)-phenyl]-1-(methoximino)-methyl}-5,6-dihydro-4H- 1,2,4-oxadiazine. MS: 89, 116, 143, 170, 201, 232, 308, 339 M$^+$.

Example (I-2)

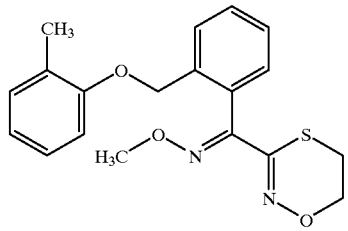

Process a)

4 g (11.2 mmol) of 2-[2-(2-methylphenoxymethyl)phenyl]-2methoximino)N-(2-hydroxyethoxy)acetamide are dissolved in 40 ml of toluene, and then 2.4 g (11.2 mmol) of phosphorus pentasulphide are added. The mixture is heated at reflux for 10 minutes, cooled rapidly and poured into water, the aqueous mixture is subjected to extraction with ethyl acetate, the extract is washed again with water and dried over magnesium sulphate, and the solvent is distilled off in vacuo. The residue is chromatographed over silica gel (eluent toluene:acetone=15:1). The product is then boiled up in ethyl acetate with activated charcoal, filtered off and concentrated. The residue obtained is 0.9 g (22% of theory) of 3-{1-[2-(2-methylphenoxymethyl)phenyl]-1-(methoximino)methyl}-5,6dihydro4H- 1,4,2-oxathiazine.
$^1$H NMR (CDCl$_3$ 2.2, 3.2, 4.0, 4.1, 5.0, 6.8–7.6 ppm).

Example (I-3)

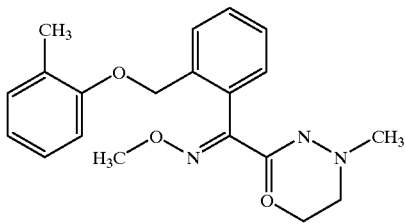

(Process b))

1.0 g (2.5 mmol) of N'-(2-chloroethyl)N'-methyl-2-methoximino-2-[2-(2-methylphenoxymethyl)phenyl]-acetic hydrazide is placed in 20 ml of anhydrous toluene, and 0.35 g (3.1 mmol) of potassium tert-butylate is added. The mixture is heated under reflux at the boiling point for 15 minutes, cooled, and washed in succession with water, dilute hydrochloric acid and again with water. The organic phase is dried over sodium sulphate and concentrated in vacuo. The residue is chromatographed on silica gel with petroleum ether/ethyl acetate (4:1). 0.39 g (45% of theory) are obtained of 2-{1-methoximino-1-[2-(2-methylphenoxymethyl)-phenyl]-methyl }-4-methyl-5,6-dihydro4H- 1,3,4oxadiazine. logP=3.54.

The compounds of the formula (I) according to the invention listed in Table 9 below are also obtained in analogy to Examples (I-1) and (I-3) and in accordance with the general description of the preparation processes according to the invention:

TABLE 9

(I)

$$Z\diagdown_{G}\diagup^{Ar}\diagdown_{E}\diagdown\overset{N-Y^2}{\underset{Y^1}{\diagup}}A$$

| Ex. No. | Z | G | Ar | E | Y² | Y¹ | A | physical constants |
|---|---|---|---|---|---|---|---|---|
| I-4 | 2,4-dimethylphenyl (CH₃ at 2, H₃C at 4) | —OCH₂— | 1,2-phenylene | CH₃ON=C | O | NH | —CH₂—CH₂— | |
| I-5 | 2,3-dimethylphenyl (CH₃ at 2, H₃C at 3) | —OCH₂— | 1,2-phenylene | CH₃ON=C | O | NH | —CH₂—CH₂— | |
| I-6 | 3-trifluoromethylphenyl (F₃C) | —OCH₂— | 1,2-phenylene | CH₃ON=C | O | NH | —CH₂—CH₂— | |
| I-7 | 4-methylphenyl (H₃C) | —OCH₂— | 1,2-phenylene | CH₃ON=C | O | NH | —CH₂—CH₂— | |

TABLE 9-continued
(I)
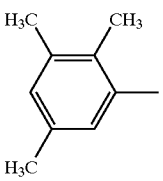
| Ex. No. | Z | G | Ar | E | Y² | Y¹ | A | physical constants |
|---|---|---|---|---|---|---|---|---|
| I-8 | 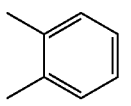 | —OCH₂— | 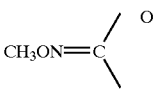 | 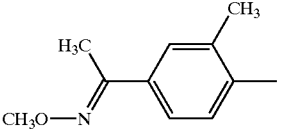 | O | NH | —CH₂—CH₂— | |
| I-9 | 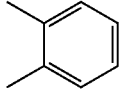 | —OCH₂— | 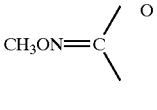 | 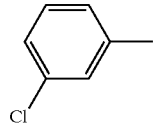 | O | NH | —CH₂—CH₂— | N M R (CDCl₃): 2.18; 2.28; 3.5; 3.91; 3.97; 5.03; 5.57; |
| I-10 | 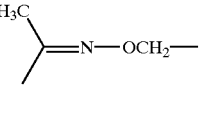 | 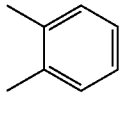 | 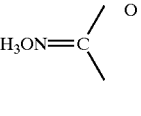 | 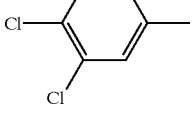 | O | NH | —CH₂—CH₂— | |
| I-11 | 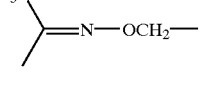 | 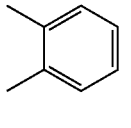 | 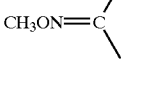 | 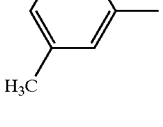 | O | NH | —CH₂—CH₂— | |
| I-12 | 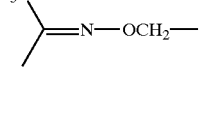 | 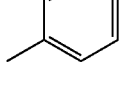 | 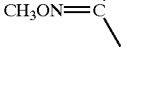 | 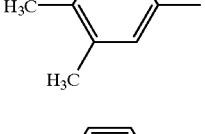 | O | NH | —CH₂—CH₂— | |
| I-13 | 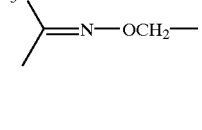 | 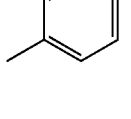 | 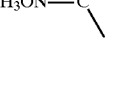 | 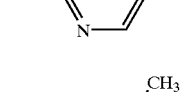 | O | NH | —CH₂—CH₂— | |
| I-14 | 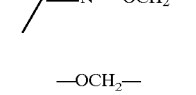 | 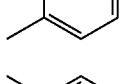 | 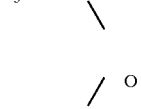 | 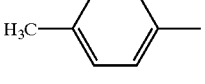 | O | NH | —CH₂—CH₂— | |
| I-15 | 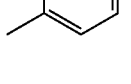 | —OCH₂— |  | 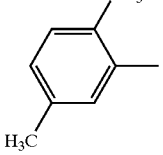 | O | S | —CH₂—CH₂— | |
| I-16 | 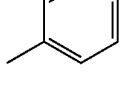 | —OCH₂— | 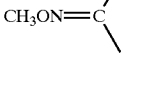 | | O | S | —CH₂—CH₂— | |

TABLE 9-continued

| Ex. No. | Z | G | Ar | E | Y² | Y¹ | A | physical constants |
|---|---|---|---|---|---|---|---|---|
| I-17 | 3-(F₃C)-phenyl | —OCH₂— | 1,2-phenylene | CH₃ON=C< | O | S | —CH₂—CH₂— | |
| I-18 | 4-(H₃C)-phenyl | —OCH₂— | 1,2-phenylene | CH₃ON=C< | O | S | —CH₂—CH₂— | |
| I-19 | 2,4,5-(H₃C)₃-phenyl | —OCH₂— | 1,2-phenylene | CH₃ON=C< | O | S | —CH₂—CH₂— | |
| I-20 | 3,4-(CH₃)₂-phenyl with C(CH₃)=NOCH₃ | —OCH₂— | 1,2-phenylene | CH₃ON=C< | O | S | —CH₂—CH₂— | |
| I-21 | 3-Cl-phenyl | H₃C-C(=N-OCH₂—) | 1,2-phenylene | CH₃ON=C< | O | S | —CH₂—CH₂— | |
| I-22 | 3,4-Cl₂-phenyl | H₃C-C(=N-OCH₂—) | 1,2-phenylene | CH₃ON=C< | O | S | —CH₂—CH₂— | |
| I-23 | 3,5-(H₃C)₂-phenyl | H₃C-C(=N-OCH₂—) | pyridyl | CH₃ON=C< | O | S | —CH₂—CH₂— | |
| I-24 | 2,4-(H₃C)₂-phenyl | H₃C-C(=N-OCH₂—) | 1,2-phenylene | CH₃ON=C< | O | S | —CH₂—CH₂— | |
| I-25 | 2-Cl-pyridin-5-yl | H₃C-C(=N-OCH₂—) | 1,2-phenylene | CH₃ON=C< | O | S | —CH₂—CH₂— | |
| I-26 | phenyl | 3-methyl-1,2,4-thiadiazol-5-yl-O— | 1,2-phenylene | CH₃ON=C< | O | NH | —CH₂—CH₂— | |

TABLE 9-continued
(I)
| Ex. No. | Z | G | Ar | E | Y² | Y¹ | A | physical constants |
|---|---|---|---|---|---|---|---|---|
| I-27 | 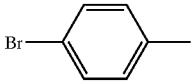 | 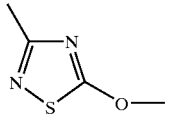 | 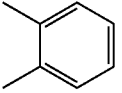 | 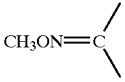 | O | NH | —CH₂—CH₂— | |
| I-28 | 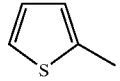 | 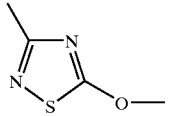 | 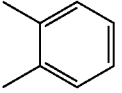 | 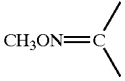 | O | NH | —CH₂—CH₂— | |
| I-29 | 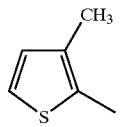 | 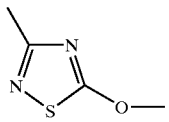 | 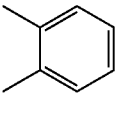 | 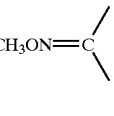 | O | NH | —CH₂—CH₂— | |
| I-30 | 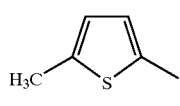 | 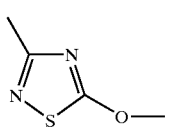 | 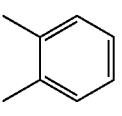 | 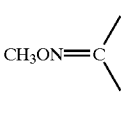 | O | NH | —CH₂—CH₂— | |
| I-31 | 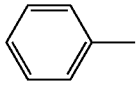 | 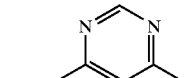 | 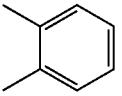 | 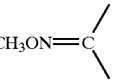 | O | NH | —CH₂—CH₂— | |
| I-32 | 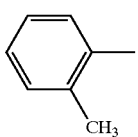 | 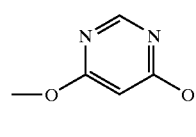 | 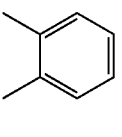 | 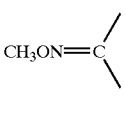 | O | NH | —CH₂—CH₂— | |
| I-33 | 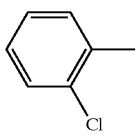 | 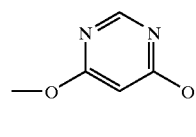 | 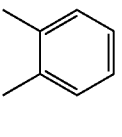 | 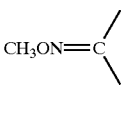 | O | NH | —CH₂—CH₂— | |
| I-34 | 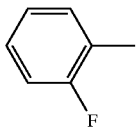 | 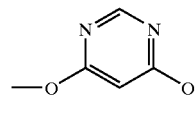 | 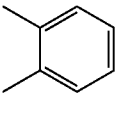 | 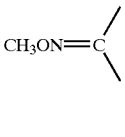 | O | NH | —CH₂—CH₂— | |
| I-35 | 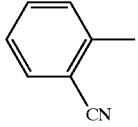 | 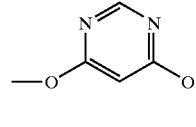 | 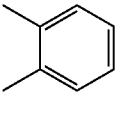 | 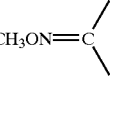 | O | NH | —CH₂—CH₂— | |
| I-36 | 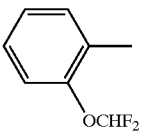 | 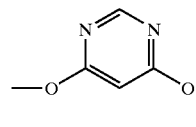 | 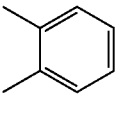 | 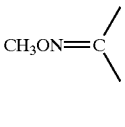 | O | NH | —CH₂—CH₂— | |

TABLE 9-continued

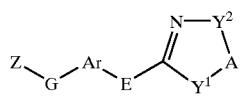
(I)

| Ex. No. | Z | G | Ar | E | Y² | Y¹ | A | physical constants |
|---|---|---|---|---|---|---|---|---|
| I-37 | phenyl | 5-F-pyrimidine-4,6-diyl-di-O- | o-phenylene | CH₃ON=C | O | NH | —CH₂—CH₂— | |
| I-38 | 2-Cl-phenyl | 5-F-pyrimidine-4,6-diyl-di-O- | o-phenylene | CH₃ON=C | O | NH | —CH₂—CH₂— | |
| I-39 | 2-CN-phenyl | 5-F-pyrimidine-4,6-diyl-di-O- | o-phenylene | CH₃ON=C | O | NH | —CH₂—CH₂— | |
| I-40 | 2-F-phenyl | 5-F-pyrimidine-4,6-diyl-di-O- | o-phenylene | CH₃ON=C | O | NH | —CH₂—CH₂— | |
| I-41 | 2-Ph-phenyl | 5-F-pyrimidine-4,6-diyl-di-O- | o-phenylene | CH₃ON=C | O | NH | —CH₂—CH₂— | |
| I-42 | 2-Cl-4-F-phenyl | 5-F-pyrimidine-4,6-diyl-di-O- | o-phenylene | CH₃ON=C | O | NH | —CH₂—CH₂— | |
| I-43 | 2,3,4,6-tetramethyl-5-(C(CH₃)=N-OCH₃)-phenyl | —OCH₂— | o-phenylene | CH₃ON=C | O | NH | —CH₂—CH₂— | |
| I-44 | 2,3-dimethyl-4-Cl-phenyl | —OCH₂— | o-phenylene | CH₃ON=C | O | NH | —CH₂—CH₂— | |

TABLE 9-continued (I)

| Ex. No. | Z | G | Ar | E | Y² | Y¹ | A | physical constants |
|---|---|---|---|---|---|---|---|---|
| I-45 | 2-chloro-4,5-dimethylphenyl-C(CH₃)=N-OCH₃ | —OCH₂— | 1,2-phenylene | CH₃ON=C< | O | NH | —CH₂—CH₂— | |
| I-46 | 2,4,5-trimethylphenyl-C(CH₃)=N-OCH₃ | —OCH₂— | 1,2-phenylene | CH₃ON=C< | O | NH | —CH₂—CH₂— | |
| I-47 | 4-ethylphenyl- | CH₃-C(=N-OCH₂—) | 1,2-phenylene | CH₃ON=C< | O | NH | —CH₂—CH₂— | |
| I-48 | 4-methylphenyl- | CH₃-C(=N-OCH₂—) | 1,2-phenylene | CH₃ON=C< | O | NH | —CH₂—CH₂— | |
| I-49 | 3-bromophenyl- | CH₃-C(=N-OCH₂—) | 1,2-phenylene | CH₃ON=C< | O | NH | —CH₂—CH₂— | |
| I-50 | 4-chloro-3-methylphenyl- | CH₃-C(=N-OCH₂—) | 1,2-phenylene | CH₃ON=C< | O | NH | —CH₂—CH₂— | |
| I-51 | 4-biphenylyl- | CH₃-C(=N-OCH₂—) | 1,2-phenylene | CH₃ON=C< | O | NH | —CH₂—CH₂— | |
| I-52 | 4-bromophenyl- | CH₃-C(=N-OCH₂—) | 1,2-phenylene | CH₃ON=C< | O | NH | —CH₂—CH₂— | |
| I-53 | 4-methoxyphenyl- | CH₃-C(=N-OCH₂—) | 1,2-phenylene | CH₃ON=C< | O | NH | —CH₂—CH₂— | |
| I-54 | 4-cyclohexylphenyl- | CH₃-C(=N-OCH₂—) | 1,2-phenylene | CH₃ON=C< | O | NH | —CH₂—CH₂— | |

TABLE 9-continued $$\underset{Z}{}\diagdown_G\diagdown_{Ar}\diagdown_E\diagdown\underset{Y^1}{\overset{N-Y^2}{\diagup}}\underset{A}{}$$
(I)

| Ex. No. | Z | G | Ar | E | Y² | Y¹ | A | physical constants |
|---|---|---|---|---|---|---|---|---|
| I-55 | phenyl-O-(p-phenylene)- | CH₃-C(=N-OCH₂-)- | o-phenylene | CH₃ON=C< | O | NH | —CH₂—CH₂— | |
| I-56 | F₂HCO-(p-phenylene)- | CH₃-C(=N-OCH₂-)- | o-phenylene | CH₃ON=C< | O | NH | —CH₂—CH₂— | |
| I-57 | F₃CS-(p-phenylene)- | CH₃-C(=N-OCH₂-)- | o-phenylene | CH₃ON=C< | O | NH | —CH₂—CH₂— | |
| I-58 | 5,6,7,8-tetrahydronaphthalen-2-yl | CH₃-C(=N-OCH₂-)- | o-phenylene | CH₃ON=C< | O | NH | —CH₂—CH₂— | |
| I-59 | 2,2-difluoro-1,3-benzodioxol-5-yl | CH₃-C(=N-OCH₂-)- | o-phenylene | CH₃ON=C< | O | NH | —CH₂—CH₂— | |
| I-60 | 3,4-difluorophenyl | CH₃-C(=N-OCH₂-)- | o-phenylene | CH₃ON=C< | O | NH | —CH₂—CH₂— | |
| I-61 | 3-fluorophenyl | CH₃-C(=N-OCH₂-)- | o-phenylene | CH₃ON=C< | O | NH | —CH₂—CH₂— | |
| I-62 | 3,4,5-trifluorophenyl | CH₃-C(=N-OCH₂-)- | o-phenylene | CH₃ON=C< | O | NH | —CH₂—CH₂— | |
| I-63 | 4-chloro-2,3-dimethylphenyl | —OCH₂— | o-phenylene | CH₃ON=C< | O | S | —CH₂—CH₂— | |
| I-64 | 4-(1-(methoxyimino)ethyl)-2,3,5-trimethylphenyl | —OCH₂— | o-phenylene | CH₃ON=C< | O | S | —CH₂—CH₂— | |

TABLE 9-continued
(I)
$$Z-G-Ar-E\underset{Y^1}{\overset{N-Y^2}{\diagdown}}\!\!\!\underset{A}{\diagup}$$
| Ex. No. | Z | G | Ar | E | Y² | Y¹ | A | physical constants |
|---|---|---|---|---|---|---|---|---|
| I-65 | 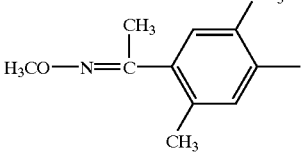 | —OCH₂— | 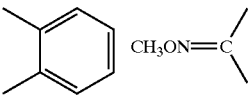 | 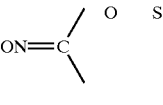 | O | S | —CH₂—CH₂— | |
| I-66 | 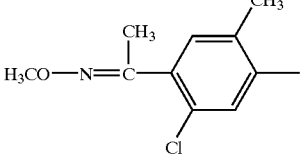 | —OCH₂— | 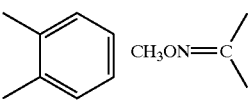 | 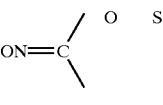 | O | S | —CH₂—CH₂— | |
| I-67 | 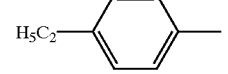 | 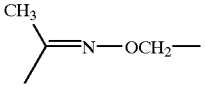 |  | 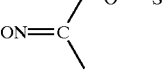 | O | S | —CH₂—CH₂— | |
| I-68 | 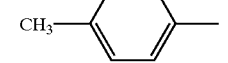 | 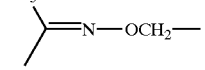 | 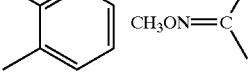 | 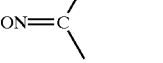 | O | S | —CH₂—CH₂— | |
| I-69 | 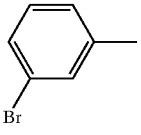 | 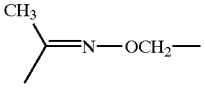 |  | 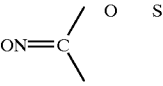 | O | S | —CH₂—CH₂— | |
| I-70 | 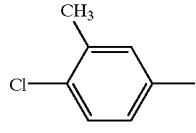 | 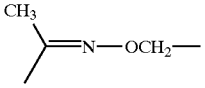 | 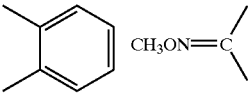 | 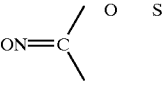 | O | S | —CH₂—CH₂— | |
| I-71 | 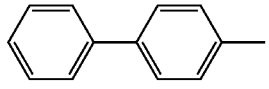 | 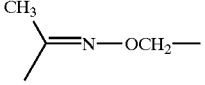 |  | 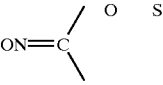 | O | S | —CH₂—CH₂— | |
| I-72 | 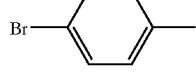 | 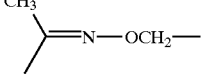 | 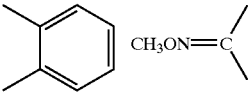 | 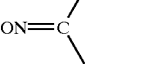 | O | S | —CH₂—CH₂— | |
| I-73 | 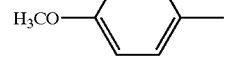 | 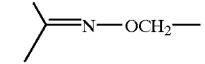 | 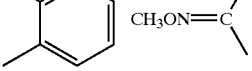 | 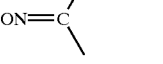 | O | S | —CH₂—CH₂— | |
| I-74 | 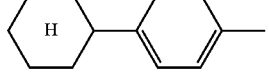 | 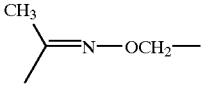 | 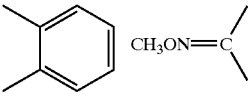 | 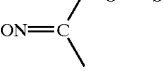 | O | S | —CH₂—CH₂— | |
| I-75 | 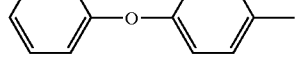 | 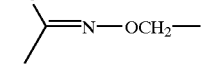 | 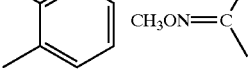 | 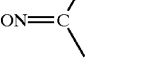 | O | S | —CH₂—CH₂— | |

TABLE 9-continued (I)

Structure: Z—G—Ar—E—[ring with N—Y², Y¹, A]

| Ex. No. | Z | G | Ar | E | Y² | Y¹ | A | physical constants |
|---|---|---|---|---|---|---|---|---|
| I-76 | F₂HCO-C₆H₄- | CH₃-C(=N-OCH₂-)- | o-C₆H₄ | CH₃ON=C< | O | S | —CH₂—CH₂— | |
| I-77 | F₃CS-C₆H₄- | CH₃-C(=N-OCH₂-)- | o-C₆H₄ | CH₃ON=C< | O | S | —CH₂—CH₂— | |
| I-78 | tetrahydronaphthyl | CH₃-C(=N-OCH₂-)- | o-C₆H₄ | CH₃ON=C< | O | S | —CH₂—CH₂— | |
| I-79 | 2,2-difluoro-benzo[1,3]dioxol-5-yl | CH₃-C(=N-OCH₂-)- | o-C₆H₄ | CH₃ON=C< | O | S | —CH₂—CH₂— | |
| I-80 | 3,4-difluorophenyl | CH₃-C(=N-OCH₂-)- | o-C₆H₄ | CH₃ON=C< | O | S | —CH₂—CH₂— | |
| I-81 | 3-fluorophenyl | CH₃-C(=N-OCH₂-)- | o-C₆H₄ | CH₃ON=C< | O | S | —CH₂—CH₂— | |
| I-82 | 3,4,5-trifluorophenyl | CH₃-C(=N-OCH₂-)- | o-C₆H₄ | CH₃ON=C< | O | S | —CH₂—CH₂— | |
| I-83 | 3-CF₃-phenyl | CH₃-C(=N-OCH₂-)- | o-C₆H₄ | CH₃ON=C< | O | S | —CH₂—CH₂— | |
| I-84 | 2-CF₃-phenyl | CH₃-C(=N-OCH₂-)- | o-C₆H₄ | CH₃ON=C< | O | S | —CH₂—CH₂— | NMR (CDCl₃): 2.26; 3.2; 3.95; 4.17; 5.17 |

*) The ¹H-NMR spectra were recorded in deuterochloroform (CDCl₃) or hexa-deuterodimethyl sulphoxide (DMSO-D₆) with tetramethylsilane (TMS) as internal standard. The value indicated is the chemical shift, δ, in ppm.

Preparation of the Starting Material Example (II-1)

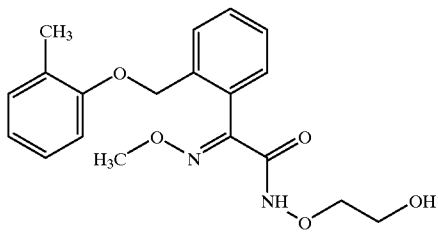

(Process a-1)

10 g (0.032 mol) of methyl 2-[2-(2-methylphenoxymethyl)phenyl]-2(methoxitnino)-acetate are dissolved in 100 ml of methanol, and then 5 g (0.064 mol) of 2-hydroxyethylhydroxylamine are added. Subsequently, 12.6 g of sodium methanolate (0.064 mol; 30% strength in methanol) are added dropwise to the reaction mixture, which is then stirred at 30° C. for 6 h, poured into water, acidified with hydrochloric acid, and subjected to extraction with ethyl acetate; the extract is washed with water and dried over magnesium sulphate and the solvent is distilled off in vacuo. The residue is chromatographed over silica gel (eluent cyclohexane: ethyl acetate initially 1:1, then 1:2). 7 g (61% of theory) are obtained of 2-[2-(2-methylphenoxymethyl)-phenyl]-2-(methoximino)-N-(2-hydroxyethoxy)-acetamide. $^1$H NMR (CDCl$_3$/TMS): δ=4.08 (s, 3H) ppm Preparation of the Starting Material Example (II-2)

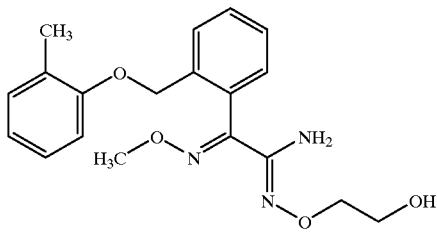

(Process a-1)

0.5 g (1.6 mmol) of ethyl 2-[2-(2-methylphenoxymethyl)-phenyl]-2-(methoximino)-acetimidate, 0.25 g (3.21 mmol) of 2-hydroxy-ethyl-hydroxylamine and 10 mg (0.19 mmol) of ammonium chloride are suspended in 5 ml of ethanol and heated at 40° C. for 16 hours. The reaction mixture is subsequently poured into 100 ml of water, acidified with 1 N hydrochloric acid to a pH of from 2 to 3 and extracted with three times 100 ml of ethyl acetate, and the organic phases are combined and dried over magnesium sulphate. After removal of the ethyl acetate by distillation under reduced pressure, the residue is chromatographed over silica gel (eluent cyclohexane:ethyl acetate=3:1). 0.43 g (69% of theory) is obtained of 2-[2-(2-methylphenoxymethyl)-phenyl]-2-(methoximino)-O-(2-hydroxyethylethyl)-acetarnidoxime. $^1$H NMR: (CDCl$_3$) 1.58, 2.27, 2.77, 3.73, 3.93, 4.0, 5.0, 5.1, 7.1–7.6 ppm.

Preparation of the Starting Material Example (II-3)

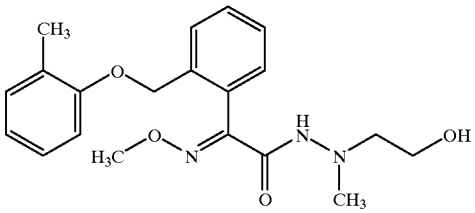

(Process a-1)

0.95 g (3 mmol) of 2-methoxyimino-2-[2-(2-methylphenoxymethyl)-phenyl]-acetyl chloride is added dropwise over the course of 20 minutes at 20° C. to a mixture of 0.23 g (3 mmol) of 2-(N-methyl-hydrazino)-ethanol and 0.42 ml (3 mmol) of tri-ethylamine in 30 ml of dichloromethane, and the mixture is stirred at 20° C. for 18 hours. The mixture is placed in water and washed first with sodium hydrogen carbonate solution and then with water. The organic phase is dried over sodium sulphate, filtered and concentrated again. The residue is chromatographed on silica gel with petroleum ether/ethyl acetate (5:1).

0.3 g (27% of theory) is obtained of N'-(2-hydroxyethyl)-N'-methyl-2-methoximino- 2-[2-(2-methylphenoxymethyl)-phenyl]-acetic hydrazide of melting point 68–69° C.

The compounds of the formula (II) according to the invention listed in Table 10 below are also obtained in analogy to Examples (II-1) to (II-3) and in accordance with the general description of the preparation processes according to the invention:

TABLE 10

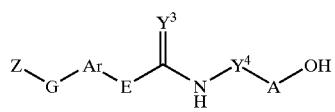

(II)

| Ex. No. | Z | G | Ar | E | Y$^3$ | Y$^4$ | A | physical constants |
|---|---|---|---|---|---|---|---|---|
| II-4 | 2,4-dimethylphenyl | —OCH$_2$— | phenyl | CH$_3$ON=C | NH | O | —CH$_2$—CH$_2$— | |

TABLE 10-continued
(II)
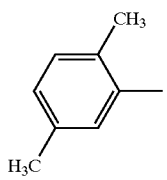
| Ex. No. | Z | G | Ar | E | Y³ | Y⁴ | A | physical constants |
|---|---|---|---|---|---|---|---|---|
| II-5 | 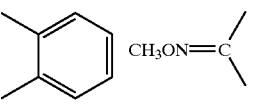 | —OCH₂— | 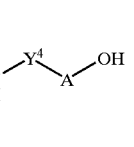 | 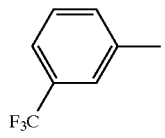 | NH | O | —CH₂—CH₂— | |
| II-6 | 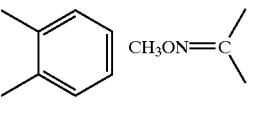 | —OCH₂— | 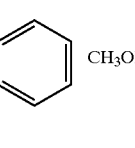 | 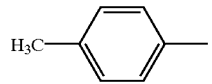 | NH | O | —CH₂—CH₂— | |
| II-7 | 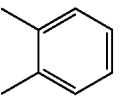 | —OCH₂— | 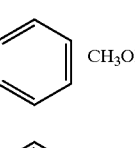 | 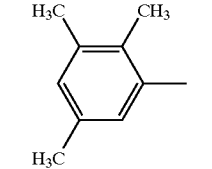 | NH | O | —CH₂—CH₂— | |
| II-8 | 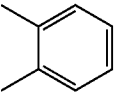 | —OCH₂— | 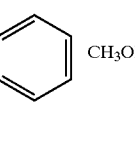 | 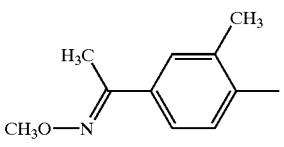 | NH | O | —CH₂—CH₂— | |
| II-9 | 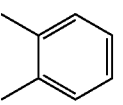 | —OCH₂— | 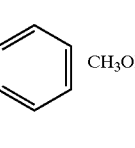 | 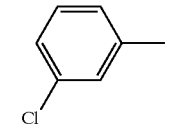 | NH | O | —CH₂—CH₂— | |
| II-10 | 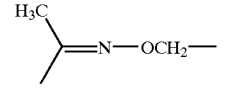 | 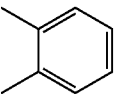 | 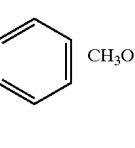 | 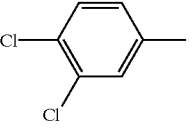 | NH | O | —CH₂—CH₂— | |
| II-11 | 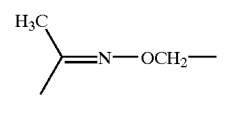 | 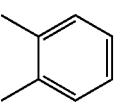 | 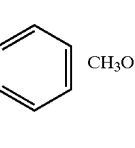 | 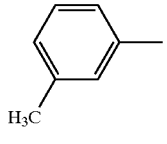 | NH | O | —CH₂—CH₂— | |
| II-12 | 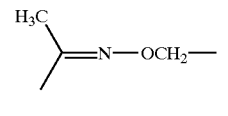 | 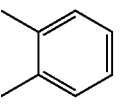 | 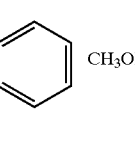 | 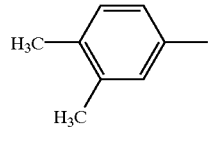 | NH | O | —CH₂—CH₂— | |
| II-13 | 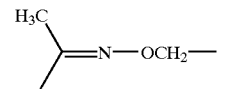 | 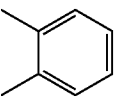 | 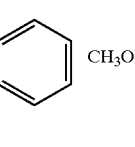 | | NH | O | —CH₂—CH₂— | |

TABLE 10-continued (II)

| Ex. No. | Z | G | Ar | E | Y³ | Y⁴ | A | physical constants |
|---|---|---|---|---|---|---|---|---|
| II-14 | 2-chloro-5-methylpyridyl | H₃C\C=N—OCH₂— | 2-methylphenyl | CH₃ON=C\ | NH | O | —CH₂—CH₂— | |
| II-15 | 3-(trifluoromethyl)phenyl | H₃C\C=N—OCH₂— | 2-methylphenyl | CH₃ON=C\ | NH | O | —CH₂—CH₂— | NMR (CDCl₃): 2.23; 3.7; 3.95; 5.14 |

*) The ¹H NMR spectra were recorded in deuterochloroform (CDCl₃) or hexa-deuterodimethyl sulphoxide (DMSO-D₆) with tertramethylsilane (TMS) as internal standard. The value indicated is the chemical shift, δ, in ppm.

Preparation of the Starting Material, Example (III-1)

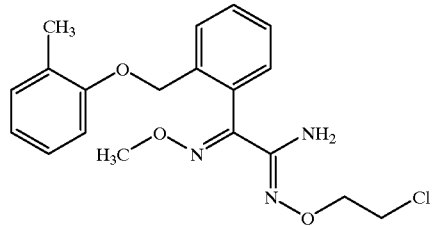

(Process b-1)

0.5 g (1.29 mmol) of 2-[2-(2-methylphenoxymethyl)-phenyl]-2-(methoxinino)-O-(2-hydroxyethyl)-acetamide oxime is dissolved in 5 ml of chloroform, and 1.5 g (12.94 mmol) of thionyl chloride are slowly added dropwise. The reaction mixture is stirred at 20° C. for 16 h and then poured into water and subjected to extraction with ethyl acetate, the extracts are washed again with water, the organic phase is dried over sodium sulphate and the solvent is distilled off under a water pump vacuum. 0.45 g (94% of theory) is obtained of 2-[2-(2-methylphenoxymethyl)-phenyl]-2-(methoximino)-O-(2-chloroethyl)acetamide oxime. MS: 116, 158, 188, 237, 268, 344, 375 M⁺.

Preparation of the Starting Material, Example (III-2)

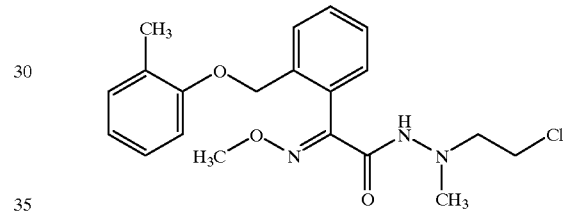

(Process b-1)

0.4 ml (5.4 mmol) of thienyl chloride is added dropwise to a solution of 1.0 g (2.7 mmol) of N'-(2-hydroxyethyl)-N'-methyl-2-methoximino-2-[2-(2-methylphenoxymethyl)-phenyl]-acetic hydrazide in 20 ml of dichloromethane. The mixture is stirred at 20° C. for 4 hours and the solvent is distilled off. The residue is dissolved in dichloromethane, and the solution is washed in succession with water, sodium hydrogen carbonate solution and again with water. The organic phase is dried over sodium sulphate and concentrated in vacuo. 1.1 g (100% of theory) are obtained of N'-(2-choroethyl)-N'-methyl-2-methoximino-2-[2-(2-methylphenoxymethyl)-phenyl]-acetic hydrazide as an oil which is employed subsequently in crude form.

¹H NMR (CDCl₃/TMS): δ=4.08 (s, 3H) ppm

The compounds of the formula (III) according to the invention listed in Table 11 below are also obtained in analogy to Examples (III-1) and (III-2) and in accordance with the general description of the preparation processes according to the invention:

TABLE 11

(III)

| Ex. No. | Z | G | Ar | E | Y¹ | Y² | A | X¹ | physical constants |
|---|---|---|---|---|---|---|---|---|---|
| III-3 | 2,4-dimethylphenyl (H₃C at 2,4) | —OCH₂— | o-phenylene | CH₃ON=C | NH | O | —CH₂—CH₂— | Cl | |
| III-4 | 2,5-dimethylphenyl | —OCH₂— | o-phenylene | CH₃ON=C | NH | O | —CH₂—CH₂— | Cl | |
| III-5 | 3-(trifluoromethyl)phenyl | —OCH₂— | o-phenylene | CH₃ON=C | NH | O | —CH₂—CH₂— | Cl | |
| III-6 | 4-methylphenyl | —OCH₂— | o-phenylene | CH₃ON=C | NH | O | —CH₂—CH₂— | Cl | |
| III-7 | 2,3,5-trimethylphenyl | —OCH₂— | o-phenylene | CH₃ON=C | NH | O | —CH₂—CH₂— | Cl | |
| III-8 | 3,4-dimethyl-α-(methoxyimino)ethylphenyl | —OCH₂— | o-phenylene | CH₃ON=C | NH | O | —CH₂—CH₂— | Cl | |
| III-9 | 3-chlorophenyl | (CH₃)₂C=N—OCH₂— | o-phenylene | CH₃ON=C | NH | O | —CH₂—CH₂— | Cl | |
| III-10 | 3,4-dichlorophenyl | (CH₃)₂C=N—OCH₂— | o-phenylene | CH₃ON=C | NH | O | —CH₂—CH₂— | Cl | |
| III-11 | 3-methylphenyl | (CH₃)₂C=N—OCH₂— | o-phenylene | CH₃ON=C | NH | O | —CH₂—CH₂— | Cl | |

TABLE 11-continued (III)

$$Z-G-Ar-E-\underset{Y^1}{\overset{\|}{C}}-\underset{H}{N}-Y^2-A-X^1$$

| Ex. No. | Z | G | Ar | E | Y¹ | Y² | A | X¹ | physical constants |
|---|---|---|---|---|---|---|---|---|---|
| III-12 | 3,5-di(H₃C)-phenyl | H₃C-C(=N-OCH₂-)- | 1,2-phenylene | CH₃ON=C< | NH | O | —CH₂—CH₂— | Cl | |
| III-13 | 6-Cl-pyridin-3-yl | H₃C-C(=N-OCH₂-)- | 1,2-phenylene | CH₃ON=C< | NH | O | —CH₂—CH₂— | Cl | |

*) The ¹H NMR spectra were recorded in deuterochloroform (CDCl₃) or hexa-deuterodimethyl sulphoxide (DMSO-D₆) with tertramethylsilane (TMS) as internal standard. The value indicated is the chemical shift, δ, in ppm.

Example A

Venturia test (apple)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism Venturia inaequalis and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example, the following compounds, (I-1) and (I-2) show, at an active compound concentration of 500 ppm, a degree of action of 100%.

Example B

Erysiphe test (barley)/protective
Solvent: 12.5 parts by weight of N-methyl-pyrrolidone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, for example, the following compounds, (I-1) and (I-2) show, at an active compound concentration of 500 ppm a degree of action of 90%.

Example C

Podosphaera test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated by dusting with conidia of the causative organism of apple mildew (Podosphaera leucotricha).

The plants are then placed in a greenhouse at 23° C. and a relative atmospheric humidity of about 70%.

Evaluation is carried out 10 days after the inoculation.

In this test, for example, the following compound (I-2) shows, at an active compound concentration of 100 ppm, a degree of action of 90%.

Example D

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are dusted with conidia of the fungus Sphaerotheca fuliginea.

The plants are then placed in a greenhouse at 23 to 24° C. and at a relative atmospheric humidity of about 75%.

Evaluation is carried out 10 days after the inoculation.

In this test, for example, the following compound (I-2) shows, at an active compound concentration of 100 ppm, a degree of action of 96%.

What is claimed is:

1. A compound of the formula

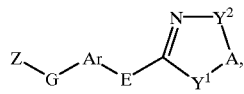
(I)

in which
A represents 1,2-ethylene;
Ar represents ortho-, meta-, or para- phenylene, which is optionally substituted by one or more substituents selected from the group consisting of fluorine, chlorine, cyano, methyl, ethyl, cyclopropyl, trifluoromethyl, ethoxy, methylthio, methylsulfinyl and methylsulfonyl;
E represents the group

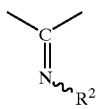

in which
$R^2$ represents methoxy or ethoxy, both of which are optionally substituted by fluorine, chlorine, cyano, methoxy, ethoxy,
G represents —C($R^4$)=N—O—CH$_2$— or T—Ar$^1$—Q—,
in which
$R^4$ represents hydrogen, cyano, methyl, ethyl or cyclopropyl,
Q represents oxygen or sulphur,
Ar$^1$ represents 1,2,4-thiadiazolediyl, 1,3,4-thiadiazolediyl, 1,2,4-oxadiazolediyl 1,3,4-oxadiazolediyl or represents pyridinediyl, pyrimidinediyl, or 1,3,5-triazinediyl, each of which is optionally substituted one or two times by identical or different substituents consisting of fluorine, chlorine, cyano, methyl, cyclopropyl, methoxy, methylthio, trifluoromethyl, difluoromethoxy, trifluoromethoxy, difluorochloromethoxy,
T represents a single bond, oxygen, sulphur, —CH$_2$—O—, —CH$_2$—S—, methylene, ethylene or propylene,
$Y^1$ represents sulphur,
$Y^2$ represents oxygen, and
Z represents phenyl, pyridyl, pyrimidyl, or thienyl, each of which is optionally substituted one to three times by identical or different substituents, the substituents being selected from the group consisting of fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methoxycarbonyl, ethoxycarbonyl, methoximinomethyl, ethoximinomethyl, methoiminoethyl, ethoximinoethyl, in each case divalent methylenedioxy or ethylenedioxy, each of which is optionally substituted one to four times by identical or different substituents consisting of fluorine, chlorine, methyl, trifluoromethyl or ethyl.

2. The compound of the formula (I) according to claim 1, in which,
A represents 1,2-ethylene;
Ar represents ortho-phenylene;
E represents the group

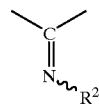

in which
$R^2$ represents methoxy,
G represents T—Ar$^1$—Q—,
in which
Q represents oxygen or sulphur,
A$^1$ represents 1,2,4-thiadiazolediyl, 1,3,4-thiadiazolediyl, 1,2,4-oxadiazolediyl 1,3,4-oxadiazolediyl or represents pyridinediyl, pyrimidinediyl, or 1,3,5-triazinediyl, each of which is optionally substituted one or two times by identical or different substituents consisting of fluorine, chlorine, cyano, methyl, cyclopropyl, methoxy, methylthio, trifluoromethyl, difluoromethoxy, trifluoromethoxy, difluorochloromethoxy,
T represents a single bond, oxygen, sulphur, —CH$_2$—O—, —CH$_2$—S—, methylene, ethylene or propylene,
$Y^1$ represents sulphur,
$Y^2$ represents oxygen, and
Z represents phenyl, pyridyl, pyrimidyl, or thienyl, each of which is optionally substituted one to three times by identical or different substituents, the substituents being selected from the group consisting of fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methoxycarbonyl, ethoxycarbonyl, methoximinomethyl, ethoximinomethyl, methoiminoethyl, ethoximinoethyl, in each case divalent methylenedioxy or ethylenedioxy, each of which is optionally substituted one to four times by identical or different substituents consisting of fluorine, chlorine, methyl, trifluoromethyl or ethyl.

3. The compound of claim 1 represented by the formula:

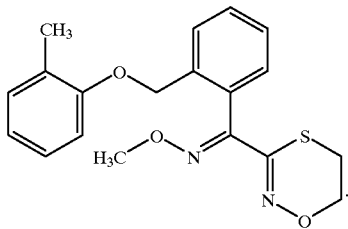

4. A pesticidal composition comprising a pesticidically effective amount of at least one compound of the formula (I) according to claim 1 and a diluent.

5. A method of combating pests comprising applying to said pests or to their habitat a pesticidally effective amount of at least one compound of the formula (I) according to claim 1.

6. The method according to claim 5, which is for combating fungi.

* * * * *